United States Patent [19]

Maltin

[11] Patent Number: 5,541,188
[45] Date of Patent: Jul. 30, 1996

[54] THERAPEUTIC APPLICATIONS OF BETA-ADRENERGIC AGONISTS

[75] Inventor: Charlotte A. Maltin, Inverurie, United Kingdom

[73] Assignee: The Rowett Research Institute, Aberdeen, Scotland

[21] Appl. No.: 426,890

[22] Filed: Apr. 24, 1995

Related U.S. Application Data

[62] Division of Ser. No. 827,839, Jan. 29, 1992, abandoned, which is a continuation of Ser. No. 266,973, Nov. 3, 1988, abandoned, which is a continuation-in-part of Ser. No. 133,702, Dec. 16, 1987, abandoned.

[30] Foreign Application Priority Data

Sep. 15, 1987 [GB] United Kingdom ............... 8721602
Feb. 17, 1988 [GB] United Kingdom ............... 8803619
Sep. 12, 1988 [EP] European Pat. Off. ............ 8830840

[51] Int. Cl.$^6$ .......................... A61K 31/52; A61K 31/135
[52] U.S. Cl. ...................... 514/263; 514/653; 514/907
[58] Field of Search ............................ 514/653, 263, 514/907

[56] References Cited

U.S. PATENT DOCUMENTS

| | | | |
|---|---|---|---|
| 3,536,712 | 10/1970 | Keck et al. | 260/253 |
| 3,574,211 | 4/1971 | Keck et al. | 260/253 |
| 3,818,011 | 6/1974 | Challier et al. | 260/268 BC |
| 3,925,475 | 12/1975 | Horrom | 260/570.8 R |
| 3,950,393 | 4/1976 | Keck et al. | 260/471 R |
| 4,119,710 | 10/1978 | Engelhardt et al. | 424/282 |
| 4,214,001 | 7/1980 | Englehardt et al. | 424/300 |
| 4,228,187 | 10/1980 | Lambelin et al. | 424/330 |
| 4,276,304 | 6/1981 | Ikezaki et al. | 424/282 |
| 4,355,045 | 10/1982 | Preston et al. | 424/322 |
| 4,404,222 | 9/1983 | Baker et al. | 424/304 |
| 4,407,819 | 10/1983 | Kiernan et al. | 424/304 |
| 4,415,564 | 11/1983 | Gamba et al. | 424/244 |
| 4,432,995 | 2/1984 | Kiernan et al. | 424/304 |
| 4,761,421 | 8/1988 | Muir | 514/352 |
| 4,847,302 | 7/1989 | Muir | 514/657 |

FOREIGN PATENT DOCUMENTS

| | | |
|---|---|---|
| 002698 | 4/1981 | European Pat. Off. . |
| 0117647 | 9/1984 | European Pat. Off. . |
| 0146738 | 7/1985 | European Pat. Off. . |
| 0170538 | 2/1986 | European Pat. Off. . |
| 67/5692 | 2/1968 | Germany . |
| 1793416 | 3/1972 | Germany . |
| 2212600 | 9/1973 | Germany . |
| 2354959 | 5/1975 | Germany . |
| 460765 | 7/1977 | Spain . |
| 1136918 | 12/1968 | United Kingdom . |
| 1178191 | 1/1970 | United Kingdom . |
| 1394542 | 5/1975 | United Kingdom . |
| 87/04618 | 8/1987 | WIPO . |
| 89/08709 | 9/1989 | WIPO . |

OTHER PUBLICATIONS

"The Effect of a Growth Promoting Drug, Clenbuterol, on Fibre Frequency and Area in Hind Limb Muscles from Young Male Rats," by C. A. Maltin M. I. Delday, and P. J. Reeds, Bioscience Reports, vol. 6, No. 3, pp. 293–299 (Jun. 2, 1986).

"Inhibition and Reversal of Denervation–Induced Atrophy by the Beta–Agonist Growth Promoteer, Clenbuterol," by C. A. Maltin, P. J. Reeds, M. I. Delday, S. M. Hay, F. G. Smith and G. E. Lobley, Bioscience Reports, vol. 6, No. 9, pp. 811–818 (Dec. 17, 1986).

"Propranolol Apparently Separates the Physical and Compositional Characteristics of Muscle Growth Induced by Clenbuterol," by C. A. Maltin, M. I. Delday, S. M. Hay, F. G. Smith and P. J. Reeds, Bioscience Reports, vol. 7, No. 1, pp. 51–57 (Jun. 19, 1987).

"The Effect of the Anabolic Agent, Clenbuterol, on Overloaded Rat Skeletal Muscle," by C. A. Maltin, M. I. Delday, S. M. Hay, F. G. Smith, G. E. Lobley and P. J. Reeds, Bioscience Reports, vol. 7, No. 2, pp. 143–149 (Aug. 3, 1987).

"The Effect of β–Agonists and Antagonists on Muscle Growth and Body Composition of Young Rats (Rattus SP.)," by P. J. Reeds, S. M. Hay, P. M. Dorward and R. M. Palmer, Comp. Biochem. Physiol., vol. 89C, No. 2, pp. 337–341, (1988).

"Clenbuterol, A Beta Agonist, Induces Growth in Innervated and Denervated Rat Soleus Muscle via Apparently Different Mechanisms," by C. A. Maltin, S. M. Hay, M. I. Delday, F. G. Smith, G. E. Lobley and P. J. Reeds, Bioscience Reports, vol. 7, No. 6, pp. 525–532, (1987).

EPO Search Report, EP Application 88308402.2 24 Jun. 1991.

"Clenbuterol, a $\beta_2$–agonist, retards atrophy in denervated muscles," by R. J. Zeman, R. Ludermann, and J. D. Etlinger, American Journal of Physiology; vol. 252, pp. E152–E155 (1987).

"Modification of body composition by clenbuterol in normal and dystrophic (mdx) mice," by N. J. Rothwell and M. J. Stock, Bioscience Reports 5, pp. 755–760 (1985).

(List continued on next page.)

Primary Examiner—Marianne M. Cintins
Assistant Examiner—William R. A. Jarvis
Attorney, Agent, or Firm—Ratner & Prestia

[57] ABSTRACT

The present invention relates to therapeutic uses of beta-adrenergic antagonists other than clenbuterol in humans and animals. The uses include retarding or reversing muscle disease such as muscular dystrophy, alleviating or reversing peripheral nervous system disease, alleviating or reversing central nervous system disease, retarding or reversing muscular atrophy of denervated muscle, alleviating or reversing loss of function arising from surgical or accidental muscular trauma, and alleviating or reversing the loss of muscle function arising from a humorally mediated catabolic state or from temporary disuse of the muscle.

8 Claims, No Drawings

OTHER PUBLICATIONS

"Chronic effects of $\beta_2$-adrenergic agonists on body composition and protein synthesis in the rat," by P. W. Emery, N. J. Rothwell, M. J. Stock, and P. D. Winter, Bioscience Reports 4, pp. 83–91 (1984).

Chemical Abstracts, vol. 102, pp. 596, (1985).

"Metabolism and Nutrition —A Repartioning Agent to Improve Performance and Carcass Composition of Broilers," by R. H. Dalrymple, P. K. Baker, P. E. Gingher, D. L. Ingle, J. M. Pensack, and C. A. Ricks, Poultry Science 63, pp. 2376–2383 (1984).

Chemical Abstracts vol. 104 (1986) (2 pages, page number unreadable).

"Effects of $\beta$-agonist (clenbuterol) on growth, carcass composition, protein and energy metabolism of veal calves," by P. E. V. Williams, L. Pagliani, G. M. Innes, K. Pennie, C. I. Harris and P. Garthwaite, British Journal of Nutrition, 57, pp. 417–428 (1987).

"Stimulation of muscle growth by clenbuterol: lack of effect on muscle protein biosynthesis," by P. J. Reeds, S. M. Hay, P. M. Dorwood, and R. M. Palmer, British Journal of Nutrition 56, pp. 249–258, (1986).

EPO Search Report, European Application 95101362.2, May 15, 1995.

D. H. Bermann, D. E. Hogue, "Effect of cimaterol and fishmeal on body composition and skeletal muscle growth in lambs," Chemical Abstracts vol. 106, pp. 546 (1987), Abstract #'s 49102f and 49103g.

$\beta_1$ Selective Adrenoceptor Antagonists. 1. "Synthesis and $\beta$-Adremergoc Blocking Activity of a Series of Binary (Arloxy) propanolamines," by R. W. Kierstead, A. Faranone, F. Mennona, J. Mullin, R. W. Guthrie, H. Crowley, B. Simko and L. C. Blaber, J. Med. Chem., pp. 1561–1569, (1983).

"Cimaterol–Induced Muscle Hypertrophy and Altered Endocrine Status in Lambs" by D. H. Beermann, W. R. Butler, D. E. Hogue, V. K. Fishell, R. H. Dalrymple, C. A. Ricks, and S. G. Scanes *J. Anim. Sci.*, 1987. vol. 65, pp. 1514–1524.

"Side Effects of Clenbuterol As a Repartitioning Agent" by J. M. Brockway, J. C. MacRae, and P. E. V. Williams. Papers and Articles, *The Veternary Record*, Apr. 18, 1987. pp. 381–383.

"Effects of Cimaterol and Fishmeal on Performance, Carcass Characteristics and Skeletal Muscle Growth in Lambs" by D. H. Beermann, D. E. Hogue, V. K. Fishell, R. H. Dalrymple, and C. A. Hicks. *J. Anim. Sci.*, 1986. vol. 62, pp. 370–380.

"Use of $\beta$–Adrenergic Agonist to Alter Muscle and Fat Deposition in Lambs" by P. K. Baker, R. H. Dalrymple, D. L. Ingle, and C. A. Ricks. *Journal of Animal Science*, vol. 59, No. 5, 1984. pp. 1256–1261.

"A Short Review and Recent New Data on the Effects of Treating Domestic Livestock With $\beta$–Agonists" by P. E. V. Williams, 1987.

"Muscle Metabolism and Real–Time Ultrasound Measurement of Muscle and Subcutaneous Adipose Tissue Growth in Lambs Fed Diets Containing a $\beta$–Agonist" by P. L. Hamby, J. R. Stouffer, and S. B. Smith. *J. Anim. Sci.*, 1986 vol. 63, pp. 1410–1417.

"The Use of $\beta$ Agonists As a Means of Altering Body Composition in Livestock Species" by P. E. V. Williams. Nutrition Abstracts and Reviews (Series B), *C.A.B. International,* Aug., 1987, vol. 57, No. 8, pp. 453–464.

"Selectivity of Clenbuterol (NAB–365) in Guinea–Pig Isolated Tissues Containing $\beta$–Adrenoceptors" by S. R. O'Donnell. *Arch. int. Pharmacodyn.* 224, pp. 190–198 (1976).

"The in vitro Actions of Clenbuterol (NAB–365) on Bovine Pulmonary Vein and Artery" by K. B. Mirbahar and P. Eyre. *J. vet. Pharmacol. Therap.* 8, pp. 202–204, 1985.

"Tolerance to or Facilitation of Pharmacological Effects Induced by Chronic Treatment With the $\beta$–adrenergic Stimulant Clenbuterol" by H. Francès, B. Diquet, P. Goldschmidt, and P. Simon. J. Neutral Transmission 62, pp. 65–76 (1985).

"Clenbuterol, A Central $\beta$–Androceptor Agonist" by H. Hall, M. Sällermark, and S. Ross. Letter to Editor, *Acta pharmacol et toxicol.*, 1980, 47, pp. 159–160.

"Does a Single Priming Injection of Clenbuterol Alter Behavioral Response to $\beta$ Androceptor Agonists and Antagonists in Mice Through a Time–Dependent Process?" by P. Martin, P. Soubrie, and Pierre Simon. European Journal of Pharmacology, 115 (1985), pp. 91–96.

"The Cardiovascular Effects of Intravenous Clenbuterol (NAB 365) and Terbutaline, Two Selective $\beta_2$Adrenoceptors and Agonists" by C. Pasotti and C. Vibelli. *Current Therapeutic Research,* vol. 25, No. 4, Apr. 1979. pp. 473–480.

"Clenbuterol ('Spiropent'): Long–Acting Bronchodilator" by D. Wheatley, M. D., E.R.C. Psych. Current Medical Research and Opinion, vol. 8, No. 2, 1982.

"Acute Bronchodilator Effect of Intravenously Injected Clenbuterol" by P. C. Curti and C. Vibelli. Current Therapeutic Research, vol. 25, No. 4, Apr., 1979. pp. 465–471.

"The Effect of the $\beta$–2–Adrenergic Agonist Clenbuterol or Implantation With Oestradiol Plus Trenbolone Acetate on Protein Metabolism in Wether Lambs" by O. Bohorov, P. J. Buttery, H. H. R. D. Correia, and J. B. Soar. *British Journal of Nutrition* (1987). 57, pp. 99–107.

Hypothesis: "Depressed Protein Synthesis is the Dominant Characteristic of Muscle Wasting and Cachexia" by M. J. Rennie, R. H. T. Edwards, P. W. Emery, D. Halliday, K. Lundholm, and D. J. Milward, Clinical Physiology, vol. 3, pp. 387–398 (1983).

"The Mode of Action of $\beta$–Agonists as Manipulators of Carcass Composition" by P. J. Buttery and J. M. Dawson. pp. 29–43, 1987.

"An Introduction to Human Pharmacology" by J. D. Graham, M.D., D.Sc., F.R.C.P., F.R.S.E. pp. 13, 16–25, 101, and 133, 1987.

THERAPEUTIC APPLICATIONS OF BETA-ADRENERGIC AGONISTS

This Application is a Divsional of U.S. application Ser. No. 827,839 filed Jan. 29, 1992, now abandoned, which is a continuation of Ser. No. 07/266,973 filed Nov. 3, 1988, abandoned, which is a continuation-in-part of application Ser. No. 133,702 filed Dec. 16, 1987, now abandoned.

This invention relates to therapeutic applications of beta-adrenergic agonists, and more particular but not exclusively to increasing the growth of innervated muscles in animals and humans, to retarding or reversing atrophy of denervated muscles in animals and humans, to alleviating or reversing the effects of various diseases in humans and animals, to modification of foetal and neonatal growth in animals and humans, and to possible genetic modification of the developing foetus of an animal or a human.

(References to "foetus" are to be taken as non-exclusively referring to the unborn offspring of humans and of non-human mammals, and to extend to the embryos of non-mammalian creatures to the extent that the substances and procedures herein described are effective.)

There are circumstances in which it is desirable that a live body comprising innervated muscles be fed so as to enhance the deposition of body protein rather than fat. Further, in a live body which has been injured by accident, disease, or surgery so that muscles are denervated, it is desirable that the usual consequential atrophy of the denervated muscles be inhibited prior to its occurrence, or reversed if atrophy has already occurred.

According to a first aspect of the invention there is provided the use of a beta-adrenergic agonist in biocompatible form, and selected to enhance one or more muscular properties comprising weight, fibre number, and protein content.

According to a second aspect of the invention there is provided a beta-adrenergic agonist in biocompatible form, and selected to reduce fat deposition from dietary input.

According to a third aspect of the invention there is provided a beta-adrenergic agonist in biocompatible form, and selected to enhance muscle growth while reducing fat deposition from dietary input.

In the first, second and third aspects of the invention, the beta-adrenergic agonist is preferably a beta sympathomimetic agent in all or part of its functions.

In the first, second, and third aspects of the invention the preferred beta-adrenergic agonist is clenbuterol, which is (4-amino-3, 5-dichlorophenyl)-2-tertbutyl-amino ethanol hydrochloride, ie a biocompatible acid addition salt of the compound whose formula is illustrated in the claim of Federal German Offenlegungsschrift 1793416.

For the purposes of one or more of the first, second and third aspects of the invention, alternative beta-adrenergic agonists are:

Isoetharine, which is 1-(3,4-dihydroxyphenol)-2-isopropyl amino ethanol hydrochloride;

Orciprenaline, which is ±-1-(3,5-dihydroxyphenyl)-2-isopropyl amino ethanol sulphate;

Reproterol, which is 7-(-((3,5, beta-trihydroxyphenyl)amino)propyl) theophylline;

Salbutamol, which is 2-tertbutylamino-1-(4-hydroxy-3-hydroxymethylphenyl) ethanol sulphate;

Terbutaline, which is 2-tert-butylamino-1-(3,5-dihydroxyphenyl) ethanol sulphate;

Fenoterol, which is 1,3, benzenediol, 5-[1-hydroxy-2-[[2-(4-hydroxyphenyl)-1-methylethyl]amino]ethyl;

Cimaterol, which is benzonitrile, 2-amino-5-[1-hydroxy-2-[(1-methylethyl)amino]ethyl]; and Ractopamine, which is [1-(4-hydroxyphenyl)-2(1-methyl-3-(4-hydroxyphenyl))propylamino]ethanol.

The invention also comprises effective analogues of the above-listed beta-adrenergic agonists.

For anabolic effects on skeletal muscle, clenbuterol is the most favoured beta-adrenergic agonist, while orciprenaline, isoetharine, fenoterol, cimaterol, and ractopamine are considered also to have significant anabolic effects in one or more forms of muscle.

For catabolic effects on body fat, clenbuterol is the most favoured beta-adrenergic agonist, while others of the listed beta-adrenergic agonists are considered also to have potentially significant catabolic effects on body fat.

Of the above-listed beta-adrenergic agonists that were specifically studied, only clenbuterol markedly increased the mass of leg muscles in tests on rats, while orciprenaline and isoetharine both produced some similar effect of lesser extent. Isoetharine and salbutamol significantly increased cardiac mass of rats, while terbutaline and reproterol reduced hepatic mass. With the exception of orciprenaline, all the beta-adrenergic agonists increased the mass of interscapular brown fat pads in rats. Orciprenaline and isoetharine increased body protein mass in rats, although not as effectively as clenbuterol. Terbutaline and orciprenaline also reduced body fat mass in rats, but not as effectively as clenbuterol. A significant relationship was discovered between decreases in body fat and hepatic mass, while changes in leg muscle mass correlated significantly with the increase in body protein.

The inventors have made a further surprising discovery in that the undesirable side-effects of the beta-adrenergic agonists that have anabolic properties can be substantially counteracted by the simultaneous use of a suitable proportion of a beta-adrenergic antagonist, preferably a mixed beta-adrenergic antagonist, but without terminating all the therapeutic properties of the beta-adrenergic agonist (some of which might be diminished without necessarily ceasing).

The beta-adrenergic antagonist may be propranolol, atenolol, or Hoffman LaRoche compound Ro 22-4574. The preferred combination is clenbuterol (or a clenbuterol analogue) and propranolol.

According to a fourth aspect of the invention there is provided a novel use of a beta-adrenergic agonist for alleviating or reversing loss of function of striated muscle arising acutely or chronically or otherwise from one or more of the following illnesses:

a. muscle disease;

b. peripheral nervous system disease;

c. central nervous system disease;

d. a humorally mediated catabolic state;

e. trauma arising from accident;

f. trauma arising from surgery;

g. atrophy arising from temporary disuse.

By way of examples of the above medical indications, the following specific indications are mentioned:

1. in respect of muscle disease; retardation of the progressive deterioration of muscular function in muscular dystrophies;

2. alleviation or reversal of neurological disease in the form of lower motor neurone—motor neurone disease, traumatic or inflammatory mononeuritides (such as radial nerve palsy, Bell's palsy, and similar illnesses), and polyneuropathy (such as Guillain-Barre Syndrome);

3. in respect of neurological disease in the form of upper motor neurone disease, limitation of wasting following cerebrovascular accidents (such as strokes) and to improve muscle function in partially paralysed limbs, and improvement of muscle bulk and muscle quality in paraplegia or quadriplegia, especially where external electrical stimulation is to be used (for example to induce walking by use of a transcutaneous or percutaneous electromyoprosthesis);

4. alleviation or retardation of cachectic conditions—in malignant diseases (including cancer cachexia) to delay deterioration in well-being associated with loss of muscle bulk, in cases of acquired immune deficiency syndrome, and to limit muscle breakdown in states of sepsis or after major trauma;

5. utilisation of muscle-specific protein anabolic effects and concomitant reduced protein gain in the gastrointestinal tract to effect a reduction of nutrient supply (particularly protein) to intestinal tumours, and thereby limit their growth;

6. in perioperative circumstances, to reduce the negative nitrogen balance and muscle protein loss associated with surgery both in a general (whole-body) sense and to limit muscle loss around operative sites, for example (i) to preserve functional muscle in elderly subjects having surgery for fractured neck of femur; (ii) to reduce risk of incisional hernias after abdominal surgery; (iii) to improve healing and rehabilitation of amputees by better preservation of functional tissue in muscle flaps;

7. limitation of atrophy arising from temporary disuse as in neurological disease (see 2 and 3 above) and in states of intentional immobilisation, for example limbs in plaster casts and thigh muscles after cartilage operations;

8. for medical benefit in the case of combined medical indications of advanced respiratory disease and poor respiratory musculature presenting together and where increased bulk of respiratory muscles may aid respiratory function, with potential double benefit if the beta-adrenergic agonist selected for beneficial effects on musculature is also a bronchodilator (as is notably the case where the beta-adrenergic agonist is clenbuterol which is indicated for treatment of bronchospasm);

9. for growth promotion in presentations of wasting illnesses such as cystic fibrosis and cerebral palsy in children (where the children tend to grow poorly and to develop little muscle).

In respect of all the medical indications comprised within the fourth aspect of the invention, the preferred beta-adrenergic agonist is clenbuterol (or an effective analogue of clenbuterol), but other beta-adrenergic agonists may alternatively or additionally be employed, such as those mentioned in connection with the first, second, and third aspects of the present invention.

According to a fifth aspect of the present invention there is provided a novel use of a beta-adrenergic agonist for use as a medicament for modifying the growth of foetal and/or neonatal animals and humans.

In the fifth aspect of the invention, the preferred beta-adrenergic agonist is clenbuterol (or an effective analogue of clenbuterol), but other beta-adrenergic agonists may be used as an alternative to (or in addition to) clenbuterol and/or clenbuterol analogues, such as those mentioned in connection with the first, second, and third aspects of the invention. It has been discovered that the administration of clenbuterol to at least one species of mammal when pregnant or lactating produces the following surprising results:

i. muscle growth is caused in the dam (female parent) despite the physiological drain of pregnancy or lactation;

ii. a reduction in muscle fibre number but a converse increase in muscle fibre size is caused in the foetal or neonatal offspring of the pregnant/lactating dam; and iii. these effects in the offspring are apparently persistent.

According to a sixth aspect of the invention there is provided a novel use of a beta-adrenergic agonist as a medicament for genetic modification of the developing foetus of an animal or human. The genetic modification which is particularly but non-exclusively intended is to affect the developing foetus at its specific stage of development at which the dystrophic gene is expressed, so as to obviate or mitigate a subsequent occurrence of muscular dystrophy. The preferred beta-adrenergic agonist in this sixth aspect of the invention is clenbuterol (or an effective analogue of clenbuterol), but other beta-adrenergic agonists may be used as an alternative to (or in addition to) clenbuterol and/or clenbuterol analogues, such as those mentioned in connection with the first, second and third aspects of the invention.

According to a seventh aspect of the invention, there is provided a method of increasing the muscular performance of a human or animal, said method comprising the step of administering to the human or animal an effective amount of a biocompatible beta-adrenergic agonist selected in accordance with the first, second or third aspects of the invention. The human or animal may be a participant in a sporting event, and such a participant may be an athlete, or a sporting animal, for example a racehorse or a greyhound. The human or animal may additionally or alternatively be desired to have improved muscular properties in a non-sporting context as, for example, in para-military situations and for draught animals. Thus the seventh aspect of the present invention differs from the other aspects of the invention in that the recipients of the "treatment" may be healthy and free of significant medical indications.

Without intent that the following postulations should have any limiting effect on the invention, it is considered that the novel response of denervated muscle to the selected beta-adrenergic agonist involves at least two mechanisms. The first mechanism involves, in the down-regulated denervated state, changes in translational efficiency and capacity which are reminiscent of the classical pleiotypic responses of cells to growth factors. The second mechanism is a specific reduction in protein breakdown. With muscles which are in the innervated state, the first mechanism is not observed because the muscles have already responded to other stimuli, whereas the second mechanism is manifested. It might be considered that the difference in response of innervated and denervated muscle to clenbuterol was associated with increased numbers of beta-adrenergic receptors in the denervated muscle membrane, but this does not appear to be the case, since even in the presence of the mixed beta-antagonist propranolol in a dose which has been shown to block the cardiac hypertrophy and the reduction in body fat, clenbuterol remains effective in reversing the muscle protein loss following denervation. This could suggest clenbuterol may be working through a different receptor to the beta-one and beta-two receptors susceptible to propranalol.

Embodiments of the invention will now be described by way of example. The following exemplary description is divided into eight sections, each dealing with a different set of effects on muscles or on muscle-related medical indications of one or more beta-adrenergic agonists (either alone or in combination with a beta-adrenergic antagonist). Each of these eight sections is further sub-divided into several headed sub-sections with self-explanatory sub-headings.

SECTION 1

The Effect of a Growth Promoting Drug, Clenbuterol, in Fibre Frequency and Area in Hind Limb Muscles from Young Male Rats

Summary

The effect of dietary administration of clenbuterol in soleus and extensor digitorum longus muscles was studied after 4 and 21 days. Both muscles showed an increase in wet weight with no significant change in total fibre number. After 4 days fibre cross-sectional areas were increased in soleus, but not in extensor digitorum longus, and after 21 days there was a change in fibre frequencies in extensor digitorum longus but not soleus muscles.

Introduction

Recently there has been considerable interest in ways of manipulating growth and enhancing the deposition of body protein rather than fat. This has led to an examination of the effect on skeletal muscle of a variety of agents which promote growth including drugs such as the beta adrenergic agonist clenbuterol.

Previous studies using clenbuterol have characteristically shown an increase in muscle growth, which has been attributed to modifications of protein turnover. Although an overall increase in muscle protein is elicited by the drug, the way in which this is expressed in terms of changes in muscle fibre number or size has not been examined. Furthermore, in other situations in which protein turnover is modified such as by insulin, it has been found that different muscles have different sensitivities to the treatment. Consequently it was of interest to establish how the growth response was expressed in skeletal muscle and whether muscles such as soleus and extensor digitorum longus with different proportions of fibre types had different sensitivities to clenbuterol.

Materials and Methods

Animals and Feeding Regime

Male Hooded-Lister rats of the Rowett strain were weaned at 19 days of age and divided into groups of 6 of equal mean weight. Initially the animals were housed in their group and offered stock rat diet (CRM nuts, Labsure, K&K Greff, Croydon, UK) ad libitum. The rats were weighed daily, and after 4 days were, if necessary, regrouped so that the groups had equal mean weights. The rats were then housed individually and fed a semi-synthetic diet (PW3: Pullar and Webster, British Journal of Nutrition, Volume 37, pages 355–363, 1977) ad libitum for 3 days. The groups of animals were then either maintained on PW3 containing no clenbuterol (control groups), or fed PW3 containing the drug at 2 mg/kg diet (clenbuterol groups). Food intake and body weights were measured daily for the study which lasted either 4 or 21 days.

Histochemistry

The animals were killed by cervical dislocation and the soleus and extensor digitorum longus muscles from the left hind limb were rapidly removed. The mid-belly portion of each muscle was isolated and oriented from transverse sectioning. The sample from each muscle was placed on a small piece of cork, surrounded with optimal cutting temperature compound, covered in talcum powder and frozen in liquid nitrogen. Serial transverse cryostat sections were cut and stained for one of the following: Ca(2+)-activated myofibrillar ATPase, nicotinamide adenine dinucleotide diaphorase, L-glucan phosphorylase or alpha-glycerophosphate dehydrogenase menadione linked. The fibre type profile of each muscle was established on the basis of the muscle staining characteristics with each of the above stains (see Table 1). Both soleus and extensor digitorum longus muscles from control rats comprised three fibre types: fast twitch glycolytic (FG); fast twitch oxidative glycolytic (FOG); and slow twitch oxidative (SO), which occurred in different proportions in each muscle type. The percentage frequency of each fibre type was estimated from a sample of no less than 200 fibres per muscle. The cross sectional area of each fibre type was measured using a Hipad digitizing tablet (Bausch and Lomb, Austin, Tex.) linked to a Prime 550 computer (Prime Computer Inc., Framingham, Mass.) programmed to calculate the area delineated on the tablet. The mean percentage area occupied by each fibre type was estimated by multiplying the mean areas of each fibre type by their percentage frequency to obtain a total, and expressing the individual products as a percentage of that total. The total number of fibres comprising the whole muscles was determined from photographic prints of whole muscle cross sections stained for myofibrillar ATPase.

Sudan black was used to stain for intramuscular lipid in muscles from both groups after 4 to 21 days on the diet.

TABLE 1

| | Histochemical description of fibre types in rat muscle | | | |
|---|---|---|---|---|
| Enzyme stained | Slow twitch oxidative (SO) | Fast twitch oxidative glycolytic (FOG) | Fast twitch glycolytic (FG) | Fast twitch oxidative (OF) |
| Ca (2+) myofibrillar ATPase | + | +++ | ++ | ++(+) |
| NADH-Diaphorase | ++ | ++(+) | + | ++ |
| alpha-Glycerophosphate dehydrogenase | + | +(+) | +++ | + |
| L-glucan phosphorylase | + | ++ | +++ | + |

Reagents

Reagents for histochemistry were obtained from Sigma (Poole, Dorset, UK), or BDH (Poole, Dorset, UK). Clenbuterol was obtained from Boehringer-Ingelheim (Bracknell, Berks., UK).

Statistics

All data are expressed as means with standard deviations. Statistical analysis was achieved by the use of a two-tailed t-Test in which, where appropriate, unequal variances could be taken into account.

Results

The muscles from clenbuterol-treated animals had a greater wet weight than those from controls (Table 2). With the exception of extensor digitorum longus muscles at 4 days ($P=0.06$), this difference was significant at both times, but the effect was most pronounced in soleus at 4 days. A study of histochemical fibre types and fibre areas in soleus and extensor digitorum longus muscles from clenbuterol-treated and control animals after 4 or 21 days on the experiment is shown in Table 2.

Soleus

After only 4 days of drug treatment there was a considerable increase in the mean cross sectional area of the fibres in muscles from clenbuterol-treated rats. This increase in size over the controls was only significant in FOG and SO fibre types: while FG fibres did appear larger than in controls, the difference was not significant. There was no difference between muscles from control and clenbuterol-treated animals with respect to either the percentage frequency or the percentage area of any of the fibre types. After 21 days on the diet there was still a difference in fibre size between control and treated groups, but it was no longer onstrated this point with the use of Sudan black staining to reveal stored lipid. In control animals the soleus muscles gave the most positive staining in accordance with their highly oxidative metabolism. Soleus muscles from clenbuterol-treated animals gave very weak staining patterns, indicating a marked reduction in stored lipid. Although a similar relationship could be shown between extensor digitorum longus muscles from control and treated groups, the difference was not so marked.

TABLE 2

(Section 1).
The effect of clenbuterol treatment on total fibre number, area and frequency in muscles of the rat

| Muscle | Wet weight (mg) | Total fibre number | Mean area (sq μm) | | | Mean % frequency | | | Mean % area | | |
|---|---|---|---|---|---|---|---|---|---|---|---|
| | | | FOG | FG | SO | FOG | FG | SO | FOG | FG | SO |
| Soleus | | | | | | | | | | | |
| Control | 64 | 3011 | 681 | 597 | 964 | 45.5 | 2.9 | 51.6 | 37.6 | 2.1 | 60.3 |
| 4 days | 8.3 | 387 | 105 | 82 | 120 | 4.0 | 1.5 | 4.6 | 5.2 | 1.2 | 6.0 |
| Clen.$^c$ | 86$^b$ | 3055 | 979$^c$ | 747 | 1201$^a$ | 43.2 | 4.5 | 52.2 | 39.2 | 3.1 | 57.7 |
| 4 days | 12.5 | 585 | 112 | 154 | 193 | 5.1 | 1.1 | 4.3 | 5.7 | 1.0 | 5.3 |
| Control | 195 | 2709 | 1658 | 1461 | 2269 | 38.1 | 4.0 | 58.0 | 32.1 | 2.9 | 65.0 |
| 21 days | 6.0 | 837 | 371 | 251 | 539 | 6.4 | 2.9 | 4.1 | 9.9 | 2.2 | 8.5 |
| Clen. | 230$^c$ | 2470 | 2196 | 2099 | 2229 | 45.2 | 2.3 | 52.5 | 44.6$^a$ | 2.5 | 53.3$^a$ |
| 21 days | 7.0 | 653 | 572 | 1110 | 471 | 7.3 | 2.4 | 6.7 | 7.9 | 2.1 | 7.9 |
| Extensor digitorum longus | | | | | | | | | | | |
| Control | 55 | 3181 | 556 | 877 | 540 | 53.5 | 45.9 | 1.2 | 42.3 | 57.0 | 1.0 |
| 4 days | 8.0 | 722 | 130 | 166 | 34 | 3.9 | 4.6 | 0.8 | 3.5 | 4.0 | 0.8 |
| Clen. | 63 | 3218 | 580 | 978 | 901$^d$ | 58.6 | 41.4 | 0.1$^d$ | 45.8 | 54.1 | 0.2$^d$ |
| 4 days | 5.0 | 514 | 74 | 84 | 138 | 5.3 | 5.2 | 0.01 | 5.0 | 5.0 | 0.1 |
| Control | 157 | 3044 | 1046 | 1723 | 864 | 56.9 | 40.6 | 2.4 | 45.5 | 52.9 | 1.6 |
| 21 days | 6.0 | 477 | 124 | 239 | 75 | 6.2 | 7.0 | 2.0 | 7.0 | 7.5 | 1.4 |
| Clen. | 179$^c$ | 3375 | 1209 | 2005 | nr | 45.6$^b$ | 54.3$^c$ | nr | 33.8$^b$ | 66.2$^c$ | nr |
| 21 days | 8.0 | 905 | 172 | 359 | | 5.2 | 5.2 | | 4.3 | 4.4 | | nr = none recorded; $^a p < 0.05$; $^b p < 0.01$; $^c p < 0.005$
All parameters are stated as means with standard deviations, n = 6 for all groups except $^d$n = 2 and $^e$n = 5 significant. Thus the observed response to clenbuterol was maximal during the first 4 days of treatment, and the subsequent growth rates between 4 and 21 days were similar in the two groups. However, the calculation of mean percentage area (reflecting functional area of one particular fibre type) at 21 days revealed a significant increase for FOG and a significant decrease for SO fibres relative to controls.

Extensor Digitorum Longus

After 4 days on the diet there was no statistically significant difference between the control and treated groups with respect to any of the parameters examined. The data for SO fibres do not merit significance owing to the small sample size: out of the 6 treated muscles examined, SO fibres were demonstrated in only two. After 21 days on the diet, the small increases in fibre areas with clenbuterol treatment were not significant, but there were significant changes in fibre type proportions. These were expressed as a statistically significant decrease in FOG frequency and an increase in FG frequency. Both changes were coupled to similar but greater changes in mean percentage areas. No SO fibres were recorded in extensor digitorum longus of treated rats, although a few were seen in controls at 21 days.

Fat Content

Following clenbuterol treatment for 4 or 21 days both muscles showed qualitatively less intramuscular fat than the equivalent controls. Investigation of muscle sections dem- Discussion The present study showed that clenbuterol increases the size and protein content of rat skeletal muscle, and revealed that the growth-promoting effects on muscle fibre area were both selective and also decreased with time. Growth promotion was evident in soleus after 4 days, but had decreased to insignificance by 21 days. It was less pronounced in extensor digitorum longus at both times.

Differences between muscles were also noted with respect to intramuscular fat. Since clenbuterol acts as a beta adrenergic agonist, the observed decrease in intramuscular fat was not unexpected. The lipolytic activity of beta agonists is documented, and other studies using clenbuterol have reported an overall decrease in body fat. However, it was striking that clenbuterol reduced the fat content of soleum much more than extensor digitorum longus. This also suggests a particular sensitivity of soleus to the action of clenbuterol, and is consistent with a positive correlation between oxidative capacity and adrenergic receptor density.

The present results suggest that the initial increase in soleus weight at 4 days was due to an increase in the size of the two predominant fibre types, FOG and SO (Table 2). However, these pronounced effects on FOG and SO fibre size seemed to be curiously specific to soleus. Although extensor digitorum longus has a considerable complement of FOG fibres and showed an increase in wet weight after 4 days, there was no significant change in fibre area of FOG or any other fibre type. Furthermore, there was no significant change in estimated total fibre number in either of the two muscle types. Thus it is probable that an increase in fibre size, rather than number, was responsible for the increase in weight of soleus. The explanation for the significant increase in wet weight of extensor digitorum longus muscles at 21 days is unclear, but the significantly increased percentage area of FOG fibres (see below), together with the trend towards more fibres, might imply an increase in total cross-sectional area of these muscles.

Observed increases in muscle wet weight have been associated with increases in muscle protein deposition. Protein deposition represents the net balance between the rates of simultaneous protein synthesis and degradation. Thus the rapid growth response in soleus can be attributed to an increase in synthesis, a decrease in degradation, or a combination of the two. In mature rats treated with clenbuterol subcutaneously, the rates of protein synthesis in gastrocnemius muscles were increased by 34% over the controls. However, in a systematic study on which the present protocol has been based (the results of which are therefore comparable to those from the present study), it has been shown that after 4 or 21 days of dietary administration of clenbuterol, there was no difference in synthesis rates in the soleus muscles of young rats compared with controls. Hence they proposed that the drug was acting to decrease the rate of degradation rather than via an effect on synthesis. This concept is interesting in the context of the present results, since it would imply that the rapid increase of fibre area in treated soleus muscles occurred through a change in protein degradation rate which was either absent or insignificant in similar fibre types from extensor digitorum longus muscles.

While extensor digitorum longus muscles did not respond significantly to treatment at 4 days, at 21 days there were significant changes in percentage frequency and percentage area of FOG and FG fibre types (Table 2). Soleus also showed significant, but apparently opposite, changes in these parameters after 21 days (Table 2). However, when considered in physiological terms the data suggest that in both muscles clenbuterol treatment led to an increase in the functional area capable of glycolytic metabolism, accompanied by a decrease in slow twitch fibres. Thus, while the growth-promoting effects of clenbuterol at first seem specific to soleus, the drug appeared to elicit changes in fibre frequency which were physiologically comparable between the two muscles. The mechanism and significance of this is unclear, but it might be speculated that clenbuterol (either directly or indirectly) not only affects growth rate by may also influence the contractile and metabolic properties of the fibres in both muscles.

SECTION 2

Inhibition and Reversal of Denervation-Induced Atrophy by the Beta-Agonist Growth Promoter, Clenbuterol

Summary

Dietary administration of the growth promoter, clenbuterol, ameliorated denervation-induced atrophy in rat soleus muscles. In acutely denervated muscles the drug inhibited the appearance of atrophy, and in chronically denervated muscles the atrophy was almost fully reversed. Responses in slow twitch oxidative fibres were particularly marked.

Introduction

Recent attention on growth promoting agents has focused on a limited number of beta2-adrenergic agonists. Previous experiments in which one of these drugs, clenbuterol, was administered orally to male weanling rats demonstrated an increase in protein deposition and a reduction in body fat with little effect on either food intake or body weight. The growth promotion appeared to be muscle-specific and the response was accompanied by an increase in fibre size. Detailed histochemical analysis showed that muscles such as soleus, in which type 1 fibres predominate, showing a more rapid and generally more marked response.

Measurements of protein turnover in young rats that had been exposed chronically to clenbuterol suggest that the action of the drug appeared to be mediated by a reduction in muscle protein degradation rather than an increase in protein synthesis. Consequently, it was of interest to establish whether a muscle which was undergoing atrophy, in which proteolysis may be increased, would still respond to the growth promoting influence of the drug. Denervation-induced atrophy was chosen for study as this form of atrophy appears to be due largely to an elevation in protein degradation.

Materials and Methods

Animals and Experimental Protocol

Male Rowett Hooded Lister Rats of the Rowett strain were weaned at 19 d post partum and divided into groups of 6 animals of equal mean weight. The initial feeding regime and the dose of clenbuterol was exactly as described previously. The animals were housed in cages with a floor of wire mesh and their body weights were measured daily. Two experiments were performed which were based on the induction of denervation atrophy in soleus muscle. The term "atrophy" is used to describe both a reduction of muscle protein content and a reduction of fibre size in comparison to the innervated control muscles.

(i) "Acute" denervation. The interaction of simultaneous denervation and administration of clenbuterol was studied to see if the drug could prevent the initiation of denervation atrophy. Rats (60±2g body weight) that had been accustomed to the control diet (PW3) for 4 days, were anaesthetized with ether and a short length (1 cm) of the left sciatic nerve was removed under aseptic conditions. Over the next 4 days the rats were offered the control diet ad libitum or the same diet to which clenbuterol (2 mg/kg) was added. The animals were then killed.

(ii) "Chronic" denervation. The second experiment was designed to test whether clenbuterol could restore growth in a muscle that was already exhibiting atrophy. Unilateral sciatic denervation was performed on animals of the same body weight as in experiment 1 and after the surgery they were offered the control diet for 3 days. At this time the animals either continued on the control diet or were offered the clenbuterol diet for a further 4 days when they were killed.

The animals were killed by cervical dislocation and the soleus muscles from both limbs were rapidly dissected, weighed and small samples from the mid-belly of the muscle were removed for histochemical analysis. The remaining muscle was frozen in liquid nitrogen and stored at −20° C. until analysed.

Histochemistry

The histochemical analysis of the muscle sections followed the same procedure as described previously. However, in these experiments fibre typing was solely based on the use of the Ca(2+)-activated myofibrillar ATPase. The soleus muscles comprised three fibre types: slow twitch oxidative (SO), fast twitch oxidative glycolytic (FOG) and fast twitch glycolytic (FG), which occurred with different frequencies. Since FG fibres occurred with a very low frequency (<5%), in the chronic denervation experiment they were omitted from estimations of area frequency and percentage area.

Determination of Muscle Protein

Weighed portions of the muscles were homogenised at 4° C. in 3 ml 0.5M perchloric acid (PCA) in a motor driven all-glass tissue grinder. The homogenate was centrifuged at 3000×g for 15 min and the precipitate was washed with a further 2 ml PCA. After centrifugation the precipitate was incubated at 37° C. in 0.3M NaOH for 1 h and portions were assayed for protein against bovine serum albumin standards.

Statistics

The significance of the differences between mean values was assessed by Student's two-tailed t-test.

Results

Experiment 1 (Table 1)

After unilateral sciatic nerve section all the animals showed a slight reduction in food intake and weight gain. This growth check was most marked in the clenbuterol-treated group and was probably due to the combination of recovery from surgery and the transient reduction in the food intake of clenbuterol-treated rats that we have noted previously. This initial growth check may explain the somewhat reduced response to clenbuterol that was observed in the innervated muscles. Nevertheless exposure to clenbuterol produced a significant increase in both the weight and protein content of the innervated soleus.

The denervated muscles were significantly lighter and contained significantly less protein than the contralateral innervated muscles of control and clenbuterol-treated rats. However, treatment with clenbuterol significantly inhibited the full expression of the denervation-related response. Thus both the weight and protein content of denervated muscles from clenbuterol-treated rats were significantly greater than those of denervated muscles from the control animals (p<0, 005).

The amelioration of the denervation-related response was particularly striking in the SO fibres. The cross-sectional area of SO fibres from denervated muscles of clenbuterol-treated animals was not significantly different from that of the SO fibres from innervated control muscles. However, while FOG fibres of denervated muscles from clenbuterol-treated animals were significantly larger (p<0.005) than the corresponding fibres in denervated muscles from untreated animals, they were still significantly smaller (p<0.01) than the corresponding fibres in innervated muscles from control animals. The differences in average fibre cross-sectional area were not accompanied by changes in the frequency of fibres of different types, but the differences in fibre areas were reflected in significant changes in the functional area accounted for by SO and FOG fibres.

Experiment 2 (Table 2)

The innervated muscles showed the expected clenbuterol-induced growth response, and denervation led to a significantly lower weight and protein content. It appeared that the effect of denervation was progressive as the denervated soleus muscles from the animals in this experiment (ie after 7 d of denervation) were lighter and contained protein than the soleus muscles after 4 d of denervation in experiment 1.

The administration of clenbuterol to these chronically denervated muscles causes a significant reversal of the atrophy. This was evident from measurements of both muscle protein content and fibre cross-sectional areas. Thus the denervated muscles from the clenbuterol-treated animals showed a statistically significant (p<0,005) increase in protein content over the untreated denervated muscles. The increase in protein was reflected by an increase in fibre area. As in experiment 1, however, SO fibres appeared to have a greater sensitivity to clenbuterol than FOG fibres. Thus, the SO fibres from denervated solei of clenbuterol-treated animals had a mean cross-sectional area which was significantly greater (p<0,005) than that of SO fibres from control denervated muscles. Indeed, the increase in SO fibre area in the denervated muscles from clenbuterol-treated animals was such that the fibre area had been nearly restored to control innervated values. The FOG fibres from denervated muscles from clenbuterol-treated animals were

TABLE 1

(Section 2)
Experiment 1-
The effect on muscle of simultaneous denervation
and administration of clenbuterol
Mean values together with 1 SD indicated in brackets

| Control | | | Clenbuterol | | |
|---|---|---|---|---|---|
| Body Weight (g) 78.7 (1.4) | | | Body weight (g) 78.6 (1.7) | | |
| Innervated Control | Denervated Control | Innervated Clenbuterol | Denervated Clenbuterol | | |
| Muscle wet weights (mg) | | | | | |
| 31 (3) | *** 24 (1) | *** 40 (2) | 31 (2) | | |
| Muscle protein (mg/g body weight) | | | | | |
| 0.080 (0.011) | *** 0.050 (0.006) | 0.086 (0.005) | ***† 0.064 (0.011) | | |
| Mean cross-sectional areas (sq μm) | | | | | |
| FOG FG SO | FOG FG SO | FOG FF SO | FOG FG SO | | |

TABLE 1-continued (Section 2)
Experiment 1-
The effect on muscle of simultaneous denervation
and administration of clenbuterol
Mean values together with 1 SD indicated in brackets

| 874 | 1085 | 368[a] | 400 | 532[a] | 970 | 900 | 1109 | 668[a] | 788 | 1069[c] |
|---|---|---|---|---|---|---|---|---|---|---|
| (134) | (40) | (68) | (95) | (113) | (61) | (142) | (63) | (80) | (247) | (132) |

Mean percentage frequencies

| 50 | 50 | 47.3 | 2 | 51.3 | 48.2 | 3 | 48.7 | 48.7 | 1.5 | 49.8 |
|---|---|---|---|---|---|---|---|---|---|---|
| (3.6) | (3.4) | (5.6) | (1) | (5.3) | (5.3) | (2.5) | (6.5) | (6.8) | (1.9) | (5.6) |

Mean percentage areas

| 45.5 | 54.0 | 40.3 | 1.3 | 56.0 | 45.8 | 2.2 | 52.0 | 38.7[b] | 2.5 | 60.8[bc] |
|---|---|---|---|---|---|---|---|---|---|---|
| (4.5) | (5.0) | (2.5) | (1) | (6.7) | (5.2) | (2.6) | (6.4) | (6.2) | (2.1) | (5.3) |

FOG = Fast twitch oxidative glcolytic; FG = fast twitch glycolytic; SO = slow twitch oxidative;
Within one fibre type, with respect to the innervated control muscles; [a] = $p < 0.005$, [b] = $p < 0.05$ and with respect to the denervated control muscle, [c] = $p < 0.005$
\*\*\*$p < 0.005$ compared with innervated control; †$p < 0.05$ compared with denervated control significantly smaller in area (p<0.005) than FOG fibres from innervated controls, but they were significantly increased in area (p<0.05) compared to FOG fibres from control denervated muscles.

If it is assumed that in this experiment the innervated and denervated muscles had initially had similar protein contents to the control animals in experiment. 1, then between 3 and 7 days after denervation the control denervated muscles lost about 1 mg of protein and the clenbuterol-treated denervated muscles gained 1.5 mg.

Experiments 1 and 2

In both experiments the cross-sectional area of FOG fibres from the innervated control muscles were observed to be greater than recorded in previous experiments. The reason for this difference is not clear; however, it is possible that denervation had imposed some postural constraints in the hind limb muscles which gave rise to this difference in fibre size.

TABLE 2

(Section 2)
Experiment 2-The effect of clenbuterol on chronically denervated muscle
Mean values together with 1 SD indicated in brackets Control 90.4 (7.8)      Clenbuterol 90.9 (2.9)
Body weight (g)

| Innervated Control | Denervated Control | Innervated Clenbuterol | Denervated Clenbuterol |
|---|---|---|---|

Muscle wet weights (mg)

| 46 (4) | \*\*\* 21 (2) | \* 51 (1) | \*\*\* 34 (1) |
|---|---|---|---|

Muscle protein (mg/g body weight)

| 0.080 (0.007) | \*\*\* 0.031 (0.005) | \* 0.089 (0.002) | ††† 0.047 (0.005) |
|---|---|---|---|

Mean cross-sectional areas (sq μm)

| FOG | FG | SO | FOG | FG | SO | FOG | FG | SO | FOG | FG | SO |
|---|---|---|---|---|---|---|---|---|---|---|---|
| 915 | 1124 | 354[a] |  | 503[a] | 1162[b] |  | 1319 | 540[ac] |  |  | 974[c] |
| (116) | (68) | (16) |  | (47) | (188) |  | (247) | (89) |  |  | (93) |

Mean percentage frequencies

| 47.1 | 52.9 | 47.8 |  | 52.2 | 46.8 |  | 53.2 | 49.8 |  |  | 50.2 |
|---|---|---|---|---|---|---|---|---|---|---|---|
| (1.0) | (1.0) | (3.7) |  | (3.7) | (4.4) |  | (4.4) | (5.8) |  |  | (5.8) |

Mean percentage areas

| 41.9 | 58.1 | 39.1 |  | 60.9 | 43.8 |  | 56.2 | 35.5 |  |  | 64.5 |
|---|---|---|---|---|---|---|---|---|---|---|---|
| (3.0) | (3.0) | (2.0) |  | (2.0) | (5.5) |  | (5.5) | (6.5) |  |  | (6.5) |

FOG = Fast twitch oxidative glcolytic; FG = fast twitch glycolytic; SO = slow twitch oxidative;
Within one fibre type, with respect to the innervated control muscles; [a] = $p < 0.005$, [b] = $p < 0.05$ and with respect to the denervated control muscle, [c] = $p < 0.005$
\*\*\*$p < 0.005$ compared with innervated control; †††$p < 0.005$ compared with denervated control

Discussion

The results from both experiments indicate that the beta-agonist clenbuterol will not only inhibit but also partially reverse denervation-induced atrophy of rat soleus muscles. The changes in muscle protein content after denervation suggest that, in the absence of clenbuterol, denervation results in an initial cessation of muscle growth but that this may then progress to a true, rather than a relative atrophy.

In experiment 1 muscle growth was blocked or severely retarded by denervation. It was not clear whether clenbuterol had inhibited a reduction in growth or whether it superimposed a growth stimulus upon a denervation-induced drive towards atrophy. In experiment 2, however, the atrophic response had been well established before the animals received the drug and here clenbuterol led to net protein deposition accompanied by an increase in fibre size in muscles that would otherwise have been atrophying.

Denervation is accompanied by an increase in the rate of protein degradation which is thought to amount largely for the reduction in muscle protein mass. It is possible that clenbuterol mediates effects on muscle by reducing protein degradation. The effect of clenbuterol on the growth response in chronically denervated muscle accords with such a mechanism.

Common to both experiments was the apparently greater sensitivity, in denervated muscle, of the SO fibres to clenbuterol treatment. The basis for this difference in sensitivity is unknown. Muscles in which SO fibres predominate have a higher fractional rate of protein turnover than muscles comprising mainly fast twitch fibres. It may be speculated that this is also true of SO fibres in comparison to other fibre types within a single muscle. If so, than an inhibition of protein degradation in a fibre with an inherently more rapid rate of protein degradation may lead to a greater response. This concept can be extended to the effects of clenbuterol on denervated muscles with their enhanced degradation rates where the proportional effects of clenbuterol on protein mass and SO fibre area were also considerably greater. Thus in experiment 2, the drug increased the protein content of innervated muscles by 12% and of denervated muscles by 50%. The proportional effect on SO fibre areas was also measurably different in innervated and denervated muscles with the increase of SO fibre area in the former being 17% but 94% in the latter.

It appears then that the process which, in normal muscle, responds to clenbuterol may become more sensitive to the drug in denervated muscles with similar controlling factors in the two states. Understanding the mechanisms of action of clenbuterol may tend to a better understanding of the controls of protein turnover and growth.

SECTION 3

Propranolol Apparently Separates the Physical and Compositional Characteristics of Muscle Growth Induced by Clenbuterol

Summary

The effect of propranolol on clenbuterol-induced changes in muscle fibre size and protein content were studied. Propranolol did not inhibit the ability of clenbuterol to stimulate protein accretion but reduced the increase in muscle fibre size. The compositional and physical characteristics of clenbuterol-induced muscle growth thus appeared to be separated by propranolol.

Introduction

The beta-adrenergic agonist, clenbuterol, has been shown to specifically promote body protein gain and to reduce body fat along with intramuscular fat. Studies in young male rats have shown that the increase in body protein is apparently confined to cardiac and skeletal muscle. In sheep the drug had an equally rapid effect on both nitrogen retention, heart rate and body temperature. However, the longer duration and greater drug sensitivity of the nitrogen retention response suggested that the two responses might have different mechanistic bases. Using a variety of adrenergic antagonists in rats, it has been found that the effects of clenbuterol on lipolysis, heart mass and energy expenditure were separable from the skeletal muscle growth response. The beta-antagonist propranolol blocked the rise in cardiac muscle mass and significantly diminished the change in body fat, but had no effect on the gross skeletal muscle growth response.

We have demonstrated in Section 1 above that the clenbuterol-induced increase in muscle protein content is expressed as muscle fibre hypertrophy. In this Section we report the effect of propranolol on the two parts of the clenbuterol-induced growth response, namely, muscle fibre size and total muscle protein content.

Material and Methods

Male Hooded Lister rats of the Rowett strain were weaned at 19 days of age and were housed in four groups of 6 animals of equal means body weight. The animals were fed to appetite a standard laboratory rat chow (Labsure CRM nuts, K and K Creff, Sussex, UK) and water was freely available at all times. After four days the animals were re-weighed and, if necessary, re-grouped so that all groups had the same mean body weight. The animals were housed singly in plastic cages with wire bottoms and fed to appetite the semi-synthetic powdered diet PW3 for a further 4 days. At this time one group was maintained on PW3 while the other groups were offered either PW3 containing clenbuterol (2 mg/kg diet), or PW3 containing propranolol (200 mg/kg diet) or PW3 containing both clenbuterol and propranolol at the doses stated above. All groups were fed their respective diet for 7 days and their weight and food intake was recorded daily.

At the end of the experimental period the animals were killed by cervical dislocation and soleus muscles removed and weighted. A small sample was removed from the mid-belly of each muscle and prepared for histochemical examination as described in Section 1. Determination of fibre type composition was based on the assessment of the staining reaction for Ca(2+)-activated myofibrillar ATPase at pH 9.4 after methanol-free formalin fixation. Those fibres which gave the most dense reaction product were designated fast twitch oxidative glycolytic (FOG) fibres, those which gave no reaction product were designated slow twitch oxidative (SO) fibres, and those which gave an intermediate reaction product were designated fast twitch glycolytic (FG) fibres. Quantitative assessments of transverse section stained for ATPase were made from photomicrographs using a Hipad digitising tablet (Bausch and Lomb, Austin, Tex.) linked to a Prime 550 computer (Prime Computers Inc., Framingham, Mass.) programmed to calculate the required parameters from the areas delineated on the tablet.

The remainder of the muscle was frozen and stored at −20° C. until used for estimations of RNA and protein. The methods used were the same as outlined above in Section 1.

Results

All the animals grew well on their respective diets and there was little difference between the mean body weights of each group at the end of the experiment (control 91.4±2.8 g, clenbuterol 94.6±4.6 g, propranolol 89.6±3.5 g, clenbuterol+propranolol 95.7±3.6 g; mean values±SEM n=6 for each group). Apart from a very slight reduction in food intake on the first day of experimental diets, the means daily intakes for each group were not significantly different (control 10.1±0.2 g, clenbuterol 9.4±0.8 g, propranolol 9.8±0.3 g, clenbuterol+propranolol 10.1±0.2 g: mean values±SEM n=6 for each group). Thus the approximate daily intake of the drug for each group was either 0.02 mg clenbuterol or 2 mg propranolol for the single drug diets or the sum of these two for the combination diet.

Muscle Protein and RNA Content (Table 1)

Dietary administration of clenbuterol gave rise to an increase in muscle weight which was accompanied by a statistically significant increase in both total protein and RNA. The addition of propranolol alone to the diet caused no change in muscle weight, total protein or RNA content. When clenbuterol and propranolol were added in combination to the diet, a significant increase in total protein content of the muscle was observed. Although the total RNA content also increased, the standard deviation of the mean was such that statistical significance was not achieved. Thus the addition of the beta-antagonist propranolol to the diet did not qualitatively alter the clenbuterol-induced growth response in rat soleus muscle. In fact the results showed that clenbuterol+propranolol caused an increase in muscle protein concentration.

TABLE 1

(Section 3)
The effect of propranolol on the clenbuterol-induced changes in protein and RNA in rat soleus muscle

|  | Control | Clen | Prop | Clen + Prop |
|---|---|---|---|---|
| Muscle Wt (mg) | 45 (4.8) | 54 (4.8) | 45 (7.3) | 51 (4.8) |
| Protein (mg/g) | 169 (13.5) | 174 (23.8) | 163 (14.2) | 191 (29.9) |
| Total Prot (mg) | 7.6 (0.8) | 9.3 (0.8)*** | 7.4 (1.3) | 9.6 (1.3)** |
| RNA (μg/g) | 2.5 (0.5) | 2.7 (0.5) | 2.4 (0.5) | 2.8 (0.7) |
| Total RNA (μg) | 113 (21.8) | 142 (20.1)* | 107 (21.8) | 142 (30.9) |
| RNA/Prot × $10^{-3}$ | 15.0 (2.5) | 15.3 (2.3) | 14.1 (2.8) | 15.0 (1.9) |

Data are presented as mean values with their standard deviations. Levels of significance determined with two-tailed Student's t test using the mean within-group standard deviations as calculated by a one-way analysis of variance; *p<0.005, p<0.01, *p<0.05 compared with control.

Muscle Fibre Area and Frequency (Table 2)

Characteristically the addition of clenbuterol to the diet of young male rats produced a skeletal muscle growth response, such that after 7 days the drug elicited fibre hypertrophy in the soleus muscles studied. Typically both FOG and SO fibre types showed a significant increase in fibre area, which together with the trend towards changes in % frequency of these two fibre types, resulted in a significant increase in FOG % area and a significant decrease in SO % area.

The muscle from rats fed a diet containing propranolol were very similar to those from control fed animals. However the addition of propranolol to the clenbuterol-containing diet resulted in a reduction of the expected clenbuterol-induced growth response. Fibre areas and frequencies measured in muscles from animals fed the combination diet did not differ significantly from those of control muscles.

TABLE 2

(Section 3)
The effect of propranolol on the clenbuterol-induced change in fibre area and frequency in rat soleus muscle

|  | Control | Clen | Prop | Clen + Prop |
|---|---|---|---|---|
| 1/8 Area (sq. μm) |  |  |  |  |
| FOG | 939 (154) | 1248 (344)* | 919 (99) | 1093 (279) |
| FG | 948 (84) | 1017 (308) | 864 (41) | 987 (146) |
| SO | 1256 (156) | 1568 (398)* | 1257 (164) | 1350 (218) |
| % Freq |  |  |  |  |
| FOG | 37.7 (8.9) | 44.4 (8.6) | 39.5 (5.0) | 39.3 (5.6) |
| FG | 2.0 (2.3) | 1.1 (1.1) | 0.6 (1.1) | 1.7 (1.5) |
| SO | 60.3 (6.9) | 54.5 (8.2) | 59.8 (5.0) | 59.0 (5.6) |
| % Area |  |  |  |  |
| FOG | 31.3 (7.2) | 39.0 (7.1)* | 32.5 (3.7) | 34.3 (5.2) |
| FG | 1.7 (2.0) | 0.9 (0.9) | 0.5 (1.0) | 1.3 (1.1) |
| SO | 67.1 (5.6) | 60.1 (6.9)* | 67.0 (3.6) | 64.4 (5.2) |

Data are presented as mean values with their standard deviations.

Fibre type nomenclature

FOG=Fast twitch oxidative glycolytic
FG=Fast twitch glycolytic
SO=Slow twitch oxidative Levels of significance determined with two-tailed Student's t test using the mean within-group standard deviations as calculated by a one-way analysis of variance; *=p<0.05, compared with control.

Discussion

The effects of the growth-promoting beta-agonists, exemplified by clenbuterol, have proved interesting in a number of respects. Clenbuterol appears to be able to stimulate a muscle-specific increase in protein deposition even in rapidly growing young male rats receiving high energy/high protein diets. Similar changes occur in denervated muscles as indicated in Section 2 above in which other agents have proved ineffective. These drugs therefore seem to circumvent a physiological constraint on muscle growth. This argument can be extended to changes in protein metabolism in that clenbuterol selectively suppresses protein degradation whereas most physiological stimuli to muscle growth simultaneously increase muscle protein synthesis and degradation.

The present results suggest that, in the short term at least, it is possible to separate the accretion of muscle protein from the normally associated increase in muscle fibre dimensions. Thus, in confirmation of previous results the presence of the mixed-beta antagonist propranolol did not inhibit the ability of clenbuterol to stimulate muscle protein accretion but reduced the increase in muscle fibre area that had been found to accompany this effect of clenbuterol treatment in previous experiments. (See Section 1 above).

It should be stressed that these are short-term experiments and that the results should not be taken to refute the ultimate correlation of muscle growth, in dimensional terms, with the accretion of muscle protein. Nevertheless, they suggest that somewhat different factors may be involved in the control of these two aspects of growth.

The separation of changes in the volume (on the assumption that muscle fibre length was the same in clenbuterol and clenbuterol+propranolol treated animals) and the changes in protein content is most simply explained by proposing that changes in muscle water had occurred. Clenbuterol alone does not increase the concentration of muscle protein but the combination of clenbuterol with the beta-blocker led to a 10% increase in muscle protein concentration. The results of a recent experiment support this proposition in showing that the water concentration was significantly ($P<0.025$) lower in the muscles of rats that had been treated with both clenbuterol and propranolol than in those of rats that had received each drug individually (clenbuterol 73.8±0.3%; propranolol, 73.3±0.3%, clenbuterol+propranolol, 71.6±0.2% mean valves ±SEM n=6 for each group).

Skeletal muscle is both a highly ordered and a heterogeneous tissue in the sense that it contains intracellular structures, such as complex sarcoplasmic and transverse tubular membrane systems and mitochondria, surrounding a highly structured myofilament array. Evidence has suggested that "intracellular" water in general and muscle water in particular does not behave as a freely mobile and exchangeable population of molecules and especially that complex interactions occur between f-actin and water. In addition the extracelluar space of skeletal muscle is constrained both by the fibrillar nature of the tissue and by the presence of the extrafilamental collagenous sheath. Consequently the relationship between the accretion and the two main components of muscle mass, protein and water, may not be as simple as that in less regularly structured tissues.

A further factor should be considered if changes in the relationship between protein and water accretion underlie the present results. In our earlier studies of the effects of propranolol on clenbuterol-stimulated growth, it was noted that while the beta-antagonist did not impair the ability of clenbuterol to stimulate muscle growth, it significantly reduced the effects of the beta-agonist on body fat and, perhaps more importantly, on total energy expenditure. One factor contributing to this increase in energy expenditure might be a beta-mediated activation of Na/K ATPase. As the activity of this enzyme is critical to the control of cellular $K+$ and $Na+$ it is probably involved in the control of water movements across the cell membrane. As a result, while clenbuterol continues to promote the deposition of protein in the presence of propranolol, the clenbuterol-induced increase in ion pumping may be blocked and the free movement of water inhibited. Whatever the underlying mechanism the changes that we have observed may be further indication that although some of the effects of clenbuterol are truly beta-mediated, the particular effects of this drug on muscle protein accretion bear little if any relationship to its action as a beta-agonist.

SECTION 4

The Effect of the Anabolic Agent, Clenbuterol, on Overloaded Rat Skeletal Muscle Summary The dietary administration of clenbuterol to young male rats has been shown to produce a muscle specific hypertrophic growth response. This section demonstrates that the combined effect of drug treatment and hypertrophic stimulus induced by tenotomy produced an additive effect on muscle growth. This effect was demonstrated in terms of both muscle composition (protein and RNA) and fibre size.

Introduction

The protein anabolic effects of the beta adrenergic agonist, clenbuterol, have aroused considered interest over the last few years. Remarkably, the drug appears to have a muscle specific action expressed as muscle fibre hypertrophy as opposed to hyperplasia (see Section 1 above).

In young rats the anabolic effect of clenbuterol appears to last for about a week and it is possible that this is because the increase in muscle size had reached a critical maximum at this stage. It was of interest, therefore, to establish whether the drug could elicit a further growth response in a muscle that had already been subjected to a separate hypertrophic stimulus. Tenotomy of gastrocnemius muscles in rats imposes an overload on the remaining functional synergists, ie the soleus and plantaris muscles which then undergo compensatory hypertrophy.

The antagonists hold the functionally overloaded muscles in a stretched state from which the hypertrophy ensues.

This section describes the effectiveness of the growth promoting drug, clenbuterol, in superimposing further growth on a muscle already subjected to a hypertrophic stimulus induced by tenotomy.

Materials and Methods

Male Weanling Hooded Lister rats from the Rowett strain were used and housed, grouped and fed as described previously (Section 1 above). In brief, the animals were divided into two groups of 18 animals of equal mean body weight. The animals were first accustomed to standard rat chow for 4 days and then to the semi-synthetic powdered diet PW3 for a further 4 days.

The tenotomy procedure was carried out under ether anaesthesia and aseptic conditions. A small incision was made in the skin at the heel and the tendons of the gastrocnemius were identified and cut. Immediately on recovery from the operative procedure, one group was offered the control diet, PW3, whilst the remaining group was offered PW3 containing clenbuterol (2 mg/kg). From each group (control and clenbuterol), 6 animals were killed after 3, 7 or 11 days and the soleus muscles were removed from both control and tenotomised limbs. The muscles were weighed and a small sample was removed from the belly of the muscle and prepared for histochemical examination as described in Section 2 above. Determination of fibre type composition was based on the Ca(2+) ATPase stain and allowed the resolution of slow twitch oxidative (SO), fast twitch oxidative glycolytic (FOG) and fast twitch glycolytic (FG) fibres. Quantitative assessment of fibre areas were made as described in Section 2 above from photomicrographs of transverse sections stained for ATPase activity.

The remainder of the muscle was frozen rapidly and stored at $-20°$ C. until used for determinations of muscle protein and RNA content using known methods.

The muscles from the four types of treatment were designated as follows:

C soleus from the untentomised limb of control fed rats.
CT soleus from the tenotomised limb of control fed rats
A soleus from the untentomised limb of clenbuterol (agonist) fed rats.
AT soleus from the tenotomised limb of clenbuterol (agonist) fed rats.

Results

Muscle Protein and RNA Content (Table 1)

In control-fed tenotomy was associated with the typical hypertrophic response in the intact synergist muscle, soleus. Muscle weight showed a statistically significant increase within 3 days after surgery, and this was accompanied by increases in muscle protein and RNA content (Table 1). Over 11 days work-induced hypertrophy increased the RNA content of group CT to a significantly higher value ($p<0.005$)

The group AT muscles showed that the effects of the drug were additive to those induced by overload. The values for protein and RNA contents in group AT muscles were significantly greater than in group A at both 7 and 11 days (Table 1).

All muscles exhibited an increase in RNA content as a result of either tenotomy, clenbuterol administration, or both, and this preceded the increase in protein gain. The effect was, however, most marked in muscles subjected to the combined treatment (group AT). Part of the clenbuterol response (group A) involved an increase in RNA, a further increase being achieved in an additive manner by the effect of tenotomy (group AT). Interestingly the CT group muscles showed the smallest increase in both total protein and RNA between 3 and 7 days, whereas in contrast, clenbuterol treated groups showed large increases in these parameters over this period.

As observed in muscles from the CT group, there was a statistically significant increase in RNA/protein ratio in muscles from the AT group from 3 days. There was no significant difference between the RNA/protein ratios in muscles from the tenotomised limbs from either dietary groups after the initial 3 day period, although both control and clenbuterol treated groups had significantly ($p<0.0005$) higher translation capacities than in either of the unoperated groups.

TABLE 1

(Section 4).
Effect of compensatory hypertrophy following tenotomy and of clenbuterol treatment on the protein and RNA content of rat soleus muscle. Data are presented as means with their standard deviations (n = 6)

|  | Unoperated limb | | Tenotomised limb | |
|---|---|---|---|---|
| Group | C | A | CT | AT |
|  | Muscle weight (mg) | | | |
| 3d | 35.0 (4.0) | 38.0 (3.4) | 44.8 (7.9)** | 44.5 (7.9)* |
| 7d | 46.0 (4.3) | 58.0 (6.7) | 54.0 (18.0) | 74.0 (7.2)***†††[c] |
| 11d | 59.0 (6.5) | 67.0 (5.3)* | 76.0 (6.2)***[c] | 83.0 (7.7)***[a] |
|  | Total protein (mg) | | | |
| 3d | 6.7 (0.9) | 7.3 (0.7) | 7.9 (1.2) | 7.7 (1.4) |
| 7d | 9.8 (1.2) | 12.3 (1.4) | 10.7 (3.6) | 14.0 (1.9)**† |
| 11d | 10.8 (0.9) | 12.4 (0.9)** | 12.5 (0.9)*** | 14.3 (0.9)***†††[a] |
|  | Total RNA (µg) | | | |
| 3d | 100 (13.2) | 121 (12.0) | 153 (27.6)***[c] | 166 (34.3)***[c] |
| 7d | 117 (12.2) | 149 (14.4) | 169 (62.6)* | 231 (31.7)***††[a] |
| 11d | 145 (21.8) | 160 (10.8) | 200 (22.3)*** | 238 (13.4)***†††[a] |
|  | RNA/protein (µg/mg) | | | |
| 3d | 15.0 (0.5) | 16.5 (0.9)* | 19.4 (0.7)***[a] | 21.4 (1.2)***†††[a] |
| 7d | 12.0 (0.9) | 12.1 (0.5) | 15.6 (2.9)*** | 16.5 (0.7)***[a] |
| 11d | 13.4 (0.9) | 12.9 (0.7) | 16.0 (1.2)***[a] | 16.7 (0.9)***[a] |

Significance values estimated with a two-tailed Student's t test using mean within-group standard deviation calculated by a one-way analysis of variance.
*$p < 0.005$; $p < 0.01$; *$p < 0.05$ compared to values from muscles from unoperated limbs of control fed animals.
†††$p < 0.005$; ††$p < 0.01$; †$p < 0.05$ compared to values from muscles from tenotomised limbs of control fed animals.
[a]$p < 0.005$; [b]$p < 0.01$; [c]$p < 0.05$ compared to values from muscles from unoperated limbs of clenbuterol fed animals than in group A muscles. Tenotomy also resulted in a significant increase ($p<0.005$) in RNA/protein ratio in the soleus muscles undergoing compensatory hypertrophy (Table 1).

Muscle Fibre Areas (Table 2)

Compensatory muscle fibre hypertrophy associated with tenotomy was evident in all fibre types in soleus muscles from control fed animals from 7 days onwards, but was statistically significant only at 11 days. The compensatory hypertrophy in group CT muscles was not significantly different from that of clenbuterol treated control muscles (group A; Table 2). The lack of statistically significant hypertrophy in the group CT and group A muscles at 3 days is unexplained and unexpected in view of the significant hypertrophy in group AT muscles.

The effects of clenbuterol and tenotomy were (in all cases except 3d) additive, such that the FOG and SO fibre areas in the AT group muscles were significantly greater than in any other group ($p<0.05$, 7d and 11d (Table 2)). A statistically significant hypertrophy was evident in the muscles from the AT group prior to that seen in comparable muscle from control fed animals. This response occurred at a time when the contralateral muscles from these clenbuterol fed animals were showing a small stimulation in weight and protein gain (Table 2). In terms of percentage change from their respective unoperated controls, however, at 11 days, the muscles from the CT group showed the greater percentage increase in fibre area, in agreement with the changes in weight and protein.

data would be consistent with the fact that compensatory hypertrophy is associated with elevated rates of protein synthesis, while clenbuterol has been shown to reduce protein degradation and have little effect on the fractional rate of synthesis. This indicated that while the net result of both treatments was similar, hypertrophy, the mechanism by which this was achieved might differ between the two.

Consequently it was not surprising that the combination of clenbuterol treatment with the tenotomy-induced hypertrophic drive ultimately (by 11 days) produced a significantly greater response ($p<0.005$) in terms of total muscle protein and RNA than either treatment alone. This response to the combined treatments was also broadly evident in the fibre sizes. The fact that the SO fibres in the muscles from the tenotomised limb were not significantly different between treatment groups may be important. From this, it can be inferred that these oxidative fibres had reached a maximum size beyond which diffusion of oxygen, sufficient for the particular metabolism of these oxidative muscles, might become limiting. The FOG and FG fibre types being capable of anaerobic metabolism would not be constrained

TABLE 2

(Section 2):
Effect of compensatory hypertrophy following tentotomy and of clenbuterol treatment on fibre area in rat soleus muscles. Data are presented as means with their standard deviations (n = 6)

| | Unoperated limb Mean area (sq μm) | | | | Tenotomised limb Mean area (sq μm) | | |
|---|---|---|---|---|---|---|---|
| | FOG | FG | SO | | FOG | FG | SO |
| 3d C | 737 (77) | 703 (50) | 996 (38) | 3d CT | 593 (40) | 566 (42) | 868 (102) |
| 3d A | 742 (217) | 628 (153) | 898 (165) | 3d AT | 918*** (163) | 918 (192) | 1286**†††[a] (180) |
| 7d C | 870 (146) | 777 (158) | 1172 (265) | 7d CT | 970 (242) | 980 (232) | 1239 (287) |
| 7d A | 1123 (195) | 1096* (263) | 1307 (159) | 7d AT | 1398***††[c] (141) | 1234*** (219) | 1672***††[c] (283) |
| 11d C | 1066 (170) | 895 (96) | 1256 (109) | 11d CT | 1328* (141) | 1130* (219) | 1661*** (283) |
| 11d A | 1337 (213) | 1153 (127) | 1487 (166) | 11d AT | 1537***†[c] (101) | 1401***†[c] (163) | 1799***[b] (118) |

Significance values estimated with a two-tailed Student's t test using the mean within-group standard deviation as calculated by a one-way analysis of variance.
*$p < 0.005$; $p < 0.01$; *$p < 0.05$ compared to values from muscles from unoperated limbs of control fed animals.
†††$p < 0.005$; ††$p < 0.01$; †$p < 0.05$ compared to values from muscles from tenotomised limbs of control fed animals.
[a]$p < 0.005$; [b]$p < 0.01$; [c]$p < 0.05$ compared to values from muscles from unoperated limbs of clenbuterol fed animals Discussion Previous studies have shown that the muscle-specific anabolic effects of clenbuterol were expressed as muscle fibre hypertrophy (Section 1 above). The results of the present experiments demonstrated that while clenbuterol treatment potentiated muscle growth, the drug does not elicit all the latent growth of which the tissue is capable.

Muscles exposed to either clenbuterol or tenotomy of their synergists exhibited hypertrophy. The response of such muscles was characterised by an increase in total muscle protein and RNA content together with an increase in fibre cross-sectional area. By 11 days, both experimental manipulations produced a comparable degree of response in terms of total protein content and fibre size. Tenotomy-induced compensatory hypertrophy, however, led to a much more marked increase in RNA/protein ratio than was evident in muscles from the clenbuterol treated group (Table 1). This to the same extent. This being so, it is possible that with the combination of the two treatments the maximum growth potential under these particular circumstances may have been realised.

SECTION 5

The Effect of Beta-agonists and Beta-antagonists on Muscle Growth and Body Composition of Young Rats (RATTUS SP.)

Summary

1. The addition of the beta-selective adrenergic agonist clenbuterol to the diet was associated with an increase in the protein and RNA of skeletal and cardiac muscle, a reduction in fat deposition and an increase in energy expenditure.

2. Neither propranolol nor atenolol blocked the effect of clenbuterol on muscle mass but both reduced its effect on cardiac and fat mass and energy expenditure.

3. Five other beta-agonists were tested. All increase the interscapular brown fat mass and lowered body fat but only two increased skeletal muscle protein.

4. It is concluded that the anabolic and anti-lipogenic actions of certain beta-agonists are mechanistically distinct.

Introduction

Some but not all beta-selective adrenergic agonists stimulate the deposition of body protein and inhibit that of body fat. Their effects have been observed in a number of species, they are effective in uncastrated male animals and, most strikingly, their anabolic properties appear to be confined to skeletal and cardiac muscle. Some results have suggested that the increase in muscle protein accretion arises from a markedly lower rate of muscle protein degradation.

It has been found that in sheep, one of these drugs, clenbuterol, administered as an abomasal infusion, increased nitrogen retention within three hours and that the increase in nitrogen retention coincided with an increase in both heart rate and body temperature. However the cardiovascular response was of short (c. 30 h) duration while nitrogen retention remained elevated for 6 weeks. The differences in the chronicities of the nitrogen retention and cardiovascular responses as well as differences in their dose sensitivities suggest that they arise from different mechanisms. In particular it might be questioned whether, if clenbuterol directly promotes muscle growth, its action in this respect is related to beta-stimulation.

In this Section we report investigations of the sensitivity to beta-antagonists of the stimulation of muscle growth and the inhibition of fat deposition by clenbuterol and of the effect of some other beta-agonists on tissue growth and fat deposition.

Materials and Methods

Materials

With the exception of Clenbuterol, which was a gift from Boehringer Ingelheim, the various drugs were obtained commercially. Materials for the assays were obtained either from Sigma Chemical Co. (Poole, Dorset, UK) or from B.D.H. PLC (Poole, Dorset, UK).

Animals and Feeding

The animals were Hooded Lister rats of the inbred Rowett strain. The animals had been bred in a specific pathogen free unit. After weaning at 19 d post partum the animals were housed in a minimal disease animal house maintained at 23° C. with a 12 hour light/dark cycle (lights on at 07.00 h). Male rats were used in experiment 1 and female rats in experiment 2. Previous work has shown that the two sexes do not differ in their responses to Clenbuterol.

After weaning the animals were housed in groups of 6 of equal mean body weight and for the next four days they were offered, to appetite, a standard laboratory diet (Labsure, K & K Greef, Croydon, Surrey, UK). They were then reweighed and if necessary regrouped so that each group had the same mean body weight at the start of the experimental period and hence had the same weight gain during the preliminary period. At this time any animals that differed from the mean by more than 2 standard deviations (±3 g) were excluded. In all 12 animals from the starting 168 were excluded on this basis.

The animals were then housed singly in clear plastic cages provided with slatted floors and allowed free access to a powdered diet (PW3) for a further 4 days after which they either continued to receive this diet or PW3 containing various drugs. The drugs were Clenbuterol, Isoetharine, Orciprenaline, Reproterol, Salbutamol, and Terbutaline. The powdered drugs were mixed in a small quantity of diet PW3 and appropriate amounts added to the main diet formulation. The diet was then mixed for at least 30 minutes at 200 revolutions per minute in a domestic food mixer using the beater attachment.

From this time their body weights (measured between 09:30 and 10:30) and food intakes (corrected for spillage) were recorded daily. Groups of animals were killed at the start of the experiment and after 7 and 21 d in experiment 1. In experiment 2 the animals were killed after 15 d.

Slaughter and Dissection

The animals were taken from the animal house at 09:00 h. They were killed by cervical dislocation no later than 3 h after transfer to the laboratory and were weighed immediately after death. The whole gastro-intestinal tract, the liver, both kidneys and the heart were removed. The organs were thoroughly blotted before weighing and the heart was exsanguinated. The hind limbs were then severed from the body, skinned and fixed to the bench by the foot. The achilles tendon was severed and the gastrocnemius/plantaris/soleus muscle group peeled proximally. The muscles were separated, each pair was pooled, placed in a tared polythene bag, weighed and frozen in liquid nitrogen. The tissues were stored in sealed bags at −20° C. until analysed within a month of dissection. The carcase was then weighed and frozen at −20° C.

Muscle Composition

The muscle samples were frozen in liquid nitrogen and powdered between 2 aluminium blocks that had been pre-cooled on solid $CO_2$. Aliquots (approximately 100 mg) of the powder were weighed accurately and homogenised in 3 ml of 0.5M Perchloric acid (PCA). The homogenate was centrifuged at 6000×g for 15 min and the pellet was resuspended in 2 ml 0.5M PCA. After centrifugation the two supernatants were pooled and stored frozen for subsequent measurement of muscle creatine content. The pellet was incubated in 10 ml 0.3M NaOH for 1 h at 37° C. and a 1 ml aliquot of the solution taken for protein measurement. The remainder was mixed with 1 ml 3M PCA, cooled to 4° C. for 30 min and centrifuged. The supernatant was taken for estimation of the RNA content from the ratio of optical density (OD) at 260 nm and 232 nm. RNA was calculated from the formula:

$$RNA\ (micro\text{-}g/ml) = 10.34\ (3.17 \times OD\ 260 - 0.75 \times OD\ 232)$$

In some experiments the pellet was then resuspended in 10 ml 0.5 ml PCA, heated for 30 min at 90° C., centrifuged and the DNA content of the supernatant estimated by a known method. All the muscles showed similar responses and therefore, for the sake of simplicity, only the results obtained in the gastrocnemius muscles are shown below.

Gross Body Composition

The frozen carcase was cut into approximately 3 cm cubes and lyophilised for 4 d, the last 2 days of which were at 40° C. The dried samples were powdered in a Braun Multimix food processor and triplicate samples were taken for analysis of nitrogen and fat. Body protein was calculated as N×62.5 and total body energy content was calculated as:

$$Energy\ (kj) = (Body\ N\ (g) \times 148.1) + (Body\ fat\ (g) \times 39.6)$$

Estimation of Muscle Mass

The measurement of total muscle mass was based on the assumption that the body pool of creatine represents almost entirely the creatine in skeletal muscle. By measuring the body content of creatine and relating this to the ratio of creatine:protein in muscle samples from the same animal an estimate of the total muscle protein pool can be obtained.

Duplicate samples of the dry powdered carcase (approximately 300 mg) were homogenised in 3 ml 0.5M PCA and then centrifuged at 6000×g for 20 min. The pellet was washed with a further 2 ml of PCA. The supernatants were combined and neutralised (pH 4–6) with a known volume of 4M KOH. After centrifugation the supernatant was re-acidified with 0.25 ml of 5.4M HCl and the solution was autoclaved for 30 min at 15 lbs/sq in. in order to convert creatine to creatinine. The creatinine concentration was measured against standards prepared from creatine treated in an identical manner. The creatine content of the PCA supernatants of gastrocnemius muscle homogenates was also estimated. Previous work in rabbits has shown that the method gives results that are indistinguishable from those obtained by total dissection.

Statistics

The significance of differences between means was assessed by two-tailed t-tests. In experiment 2 changes in body fat, hepatic, cardiac and total muscle mass were related to one another by the Spearmann Rank Correlation test. A value of P (two-tailed) less than 0.05 was taken as being statistically significant.

Results

Experiment 1. The Effects of Beta-antagonists on Clenbuterol Action

Although the presence of clenbuterol in the diet had no effect on food intake it was associated with an increase in the protein and RNA (but not the DNA) contents of the gastrocnemius muscle (Table 2) and an increase in the total muscle protein mass (Table 3). Rather than decreasing this effect of clenbuterol both antagonists produced a further small, but statistically significant increase in gastrocnemius protein content. Cardiac protein, RNA and DNA were also higher in animals that had received clenbuterol alone. However both propranolol and atenolol significantly reduced the effect of clenbuterol on the protein and RNA content of the heart.

Body protein, fat and calculated energy expenditure

Four observations were noteworthy (Table 3). First, the effect of clenbuterol on both total body and total muscle protein associated with clenbuterol treatment was largely complete by 7 d of treatment. Second, the increase in total body protein was entirely accounted for by the increase in muscle protein mass. Third, neither of the antagonists impaired the effect of clenbuterol on total muscle and total body protein deposition and again there was a tendency (although not significant) for total muscle protein to be higher in groups CP, CPII and CA. Fourth, the lower rate of fat deposition associated with the prolonged ingestion of clenbuterol was partially reversed by both propranolol and atenolol. It should be noted that this effect was not completely revered, and the body fat mass of groups CP, CPII and CA was still significantly lower than that of the control animals.

When based on the difference between metabolizable energy intake and body energy gain it appeared that clenbuterol increased total energy expenditure by about 8% (P<0.001) and that both antagonists completely reversed this effect of the beta-agonist.

Experiment 2. The Effects of Beta(2)-agonists on Growth and Body Composition

Of the agonists studied only clenbuterol markedly increased the mass of the leg muscles (Table 4). Although orciprenaline and isoetharine both produced some effect this was less than that associated with clenbuterol treatment. Isoetharine and salbutamol increased cardiac mass significantly and terbutaline and reproterol reduced the hepatic mass. With the exception of orciprenaline all the drugs increased the mass of the interscapular brown fat pads.

Orciprenaline and isoetharine increased body protein mass (+5% P<0.05) although not as effectively as clenbuterol (+11% P<0.001). Terbutaline and orciprenaline also reduced body fat mass (−14%) but again neither drug had as marked an effect as clenbuterol (−26%). The Spearmann Rank Correlation test revealed a significant relationship between the decreases in body fat and hepatic mass (R=0.421: P<0.05). The change in leg muscle mass correlated significantly with the increase in body protein but with no other measurement.

Discussion

Although a lower rate of fat deposition has been a common finding in animals treated with a variety of both alpha and beta selective adrenergic agonists, only a few beta-agonists increase body protein. Therefore it might be questioned whether the apparently interrelated effects of clenbuterol, fenoterol and cimaterol on body protein and fat share a common, beta-mediated mechanism.

The present results in clenbuterol treated animals confirmed our previous findings that the growth-promotion appeared to be confined to skeletal muscle protein and RNA were not accompanied by increases in DNA suggesting that the growth response was hypertrophic rather than hyperplastic in nature. This has been confirmed by measurements of fibre number and diameter as shown in Section 1 above. In heart, however, there was an increase in DNA content.

The transient nature of the effect of clenbuterol on muscle growth might be interpreted as indicating a tachyphylaxis. However the drug had a progressive effect on cardiac protein (increased by 14 mg at 7 d and by 35 mg at 21 d) and on fat mass (reduced by 2.5 g at 7 d and by 8.7 g at 21 d) and this suggests that tachyphylaxis is not the explanation. It is possible that the cessation of accelerated muscle growth results from an eventual limitation imposed by an unaltered rate of skeletal growth. Sheep and cattle, in which the effect of clenbuterol on body nitrogen gain is much more prolonged, have a much lower weight-specific growth rate.

Neither the mixed-beta antagonist propranolol nor the beta(1)-selective antagonist atenolol blocked the effect of clenbuterol on muscle growth. Furthermore in preliminary work with a beta(2)-antagonist—Hoffman La Roche compound Ro 22-4574—we were also unable to find any inhibitory action on clenbuterol-stimulated muscle growth. In fact the beta-antagoniststended to produce a further small increase in muscle protein deposition. It is possible that the effects of clenbuterol on body fat, intramuscular fat, and muscle glycogen might place some limitation on muscle growth. By reducing these "deleterious" effects of clenbuterol the beta-antagonists may have thereby reduced their inhibitory effects on muscle growth.

These results contrasted with the substantial inhibition by both antagonists of the effect of clenbuterol on energy expenditure and cardiac growth and their partial inhibition of the effect of clenbuterol on body fat deposition. In sheep we have noted a marked effect of clenbuterol on heart rate, an effect that coincided with a reduction in nitrogen excretion. However these two effects had different dose sensitivities (nitrogen retention being the more sensitive) and chronicities (the increase in heart rate being a transient phenomenon) and these observations suggested that they might not be directly mechanistically related. As both the increase in cardiac growth and total energy expenditure associated with clenbuterol treatment were blocked by the beta(1)-selective antagonist atenolol, it is possible that the increase in cardiac growth is a beta(1)-mediated response and that it results from cardiac overload, rather than from the direct action of clenbuterol as an anabolic agent.

Some degree of caution should be exercised. It remains possible that the differential responses of muscle growth on the one hand, and of fat deposition and cardiac growth on the other merely result from differences in the affinity of the appropriate beta receptors to clenbuterol and propranolol. To investigate this possibility we exposed rats to the high dose of propranolol for 4 days before exposing them to clenbuterol and propranolol. Again the antagonist did not block the effect of clenbuterol on muscle growth [Gastrocnemius protein content (mg); Control, 288±9; Clenbuterol+Propranolol, 392±12].

The results obtained with the other beta-agonists also demonstrate the complex pharmacology of the growth response. The drugs were selected initially for differences in their absolute potencies and beta(2) selectivities. Although they were administered at twice the dose of clenbuterol none were as effective as clenbuterol in promoting muscle growth. Salbutamol and orciprenaline significantly decreased body fat, 4 of the 5 drugs increased the mass of the brown fat pads and all tended to reduce hepatic mass, an effect that they shared with clenbuterol. Significant Rank Correlations between the effects of the drugs on cardiac, hepatic and fat mass were found but, with the exception of body protein mass, the change in leg muscle mass did not significantly correlate with any of the other measurements. Once again therefore the effects of the drugs on muscle growth and their effects on body fat and cardiac mass were separated.

Although the results cast doubt on a close relationship between beta activity and the stimulation of muscle growth they offer no explanation as to the mechanisms of the anabolic action. Our previous results suggest that clenbuterol increases muscle protein deposition by reducing the rate of muscle protein degradation. This mechanism is different from that underlying the promotion of muscle growth by change in tension, workload and insulin. Furthermore it is not certain whether the effect of clenbuterol on muscle protein deposition is direct or whether it is related to some other hormonal change. It is of interest that the non-selective beta-agonist isoproteronol reduces protein degradation in isolated muscles and in the hemi-corpus preparation but we have been unable to demonstrate a similar effect of clenbuterol (over the range $10^{-11}$M to $10^{-8}$M) in isolated muscles. Nevertheless clenbuterol at concentrations in excess of $10^{-10}$M reduced muscle glycogen in vitro. It is possible that a hitherto unidentified metabolite of clenbuterol is responsible for the stimulation of muscle growth while changes in fat deposition, glycogenolysis and energy expenditure are direct, beta-mediated, responses to the drug itself.

TABLE 1

(Section 5):
Designation of the diets offered to the animals

| Diet group | Addition to the diet |
| --- | --- |
| C | None |
| CL | Clenbuterol (2 mg/kg) |
| P | Propranolol (20 mg/kg) |
| PIII | Propranolol (200 mg/kg) |
| CP | Clenbuterol (2 mg/kg) + Propranolol (20 mg/kg) |
| CPII | Clenbuterol (2 mg/kg) + Propranolol (200 mg/kg) |
| A | Atenol (20 mg/kg) |
| CA | Clenbuterol (2 mg/kg) + Atenolol (20 mg/kg) |
| T | Terbutaline (4 mg/kg) |
| O | Orciprenaline (4 mg/kg) |
| R | Reproterol (4 mg/kg) |
| S | Salbutamol (4 mg/kg) |
| I | Isoetharine (4 mg/kg) |

TABLE 2

(Section 5)
The protein, RNA and DNA contents of the gastrocnemius muscles and the heart of male rats at the end of a 21-day period over which they received a control diet or one of the diets that are listed in Table 1. Mean values together with one standard error of the mean for the numbers indicated.

| Group | N | Gastrocnemius Muscle Protein (mg) | RNA (μg) | DNA (μg) | Cardiac Muscle Protein (mg) | RNA (μg) | DNA (μg) |
|---|---|---|---|---|---|---|---|
| C | 18 | 282 ± 5 | 2340 ± 60 | 810 ± 39 | 138 ± 3 | 1580 ± 30 | 1256 ± 20 |
| P | 12 | 272 ± 5 | 2350 ± 50 | ND | 129 ± 4 | 1580 ± 30 | ND |
| PII | 6 | 290 ± 5 | 2340 ± 90 | 818 ± 48 | 144 ± 3 | 1630 ± 40 | 1264 ± 30 |
| A | 12 | 289 ± 9 | 2360 ± 50 | ND | 131 ± 6 | 1660 ± 50 | ND |
| CL | 18 | 312 ± 3*** | 2540 ± 50*** | 756 ± 47 | 164 ± 5*** | 1780 ± 30*** | 1310 ± 20* |
| CP | 12 | 315 ± 4*** | 2490 ± 40* | ND | 144 ± 3†† | 1620 ± 50† | ND |
| CPII | 6 | 320 ± 3***, @ | 2550 ± 70*** | 776 ± 42 | 145 ± 5† | 1690 ± 40† | 1305 ± 30 |
| CA | 12 | 338 ± 8***, @ | 2620 ± 40 | ND | 141 ± 4†† | 1700 ± 30*, † | ND |

The statistical significance of differences are indicated:
Significantly higher than group C, *$P < 0.05$; ***$P < 0.001$
Significantly lower than group CL, †$P < 0.05$; ††$P < 0.01$
Significantly higher than group CL, @$P < 0.05$

TABLE 3

(Section 5)
Total body and muscle protein, body fat and calculated energy expenditure of young male rats offered to appetite for 7 or 21 days a control diet or the diets that are described in Table 1. Mean values together with one standard error of the mean for the numbers indicated.

| Day | Group | N | Body Protein (g) | Muscle Protein (g) | Body Fat (g) | Total Energy Expenditure (kj) |
|---|---|---|---|---|---|---|
| 0 | IS | 9 | 7.5 ± 0.2 | 2.8 ± 0.1 | 3.8 ± 0.3 | — |
| 7 | C | 6 | 15.9 ± 0.5 | 7.3 ± 0.3 | 10.5 ± 0.7 | 855 ± 28[b] |
|  | P | 6 | 16.3 ± 0.4 | 7.7 ± 0.2 | 9.9 ± 0.5 | 859 ± 24 |
|  | CL | 6 | 18.0 ± 0.77*** | 9.4 ± 0.3*** | 8.0 ± 0.5†† | 912 ± 10* |
|  | CP | 6 | 17.8 ± 0.5*** | 9.4 ± 0.5*** | 9.4 ± 0.4 @ | 858 ± 14† |
| 21 | C | 18 | 30.5 ± 0.5 | 15.2 ± 0.4 | 22.6 ± 1.1 | 3327 ± 41[c] |
|  | P | 12 | 30.9 ± 0.5 | 15.7 ± 0.4 | 19.8 ± 0.5 | 3366 ± 63 |
|  | PII | 6 | 30.2 ± 0.6 | 14.9 ± 0.4 | 20.2 ± 1.8 | 3310 ± 112 |
|  | A | 12 | 31.1 ± 0.5 | 16.1 ± 0.6 | 21.5 ± 1.7 | 3494 ± 101 |
|  | CL | 18 | 32.8 ± 0.5*** | 18.0 ± 0.4*** | 13.9 ± 0.4††† | 3716 ± 53*** |
|  | CL | 12 | 33.9 ± 0.5*** | 19.2 ± 0.7*** | 17.8 ± 0.6††, @@ | 3420 ± 49 |
|  | CPII | 6 | 32.7 ± 0.5*** | 18.2 ± 0.6*** | 18.2 ± 0.6††, @@ | 3125 ± 70†† |
|  | CA | 12 | 33.2 ± 0.5*** | 18.2 ± 0.4*** | 17.6 ± 0.9††, @@ | 3385 ± 55 |

[a]Animals slaughtered on the day of first exposure to the experimental diets.
[b]Energy expenditure from 0–7 days
[c]Energy expenditure from 7 to 21 days
The statistical significance of the differences are indicated:
Significantly higher than group C, ***$P < 0.001$
Significantly lower than group CL, ††$P < 0.01$; †††$P < 0.001$
Significantly higher than group CL, @$P < 0.05$; @@$P < 0.01$

TABLE 4

(Section 5):
Tissue weights (mg), body protein (g) and body fat (g) of groups of 6 female rats offered to appetite for 15 days control diet or the diets described in Table 1. Mean values together with a common estimate of variance pooled standard deviation PSD

| Tissue | Group C | CL | T | R | I | S | O | PSD |
|---|---|---|---|---|---|---|---|---|
| Liver | 7370 | 6530††† | 6750†† | 6950† | 6980 | 7000 | 7150 | 344 |
| Heart | 654 | 818*** | 653 | 669 | 724* | 729* | 709 | 48 |

TABLE 4-continued (Section 5):
Tissue weights (mg), body
protein (g) and body fat (g) of groups of 6 female rats offered to appetite
for 15 days control diet or the diets described in Table 1. Mean values
together with a common estimate of variance pooled standard deviation PSD

| Tissue | Group | | | | | | | |
|---|---|---|---|---|---|---|---|---|
| | C | CL | T | R | I | S | O | PSD |
| Muscle[a] | 1841 | 2144*** | 1822 | 1886 | 1921* | 1876 | 1960* | 94 |
| Brown Fat | 448 | 524** | 449*** | 511* | 524** | 531** | 434 | 60 |
| Body Protein | 24.0 | 26.7*** | 23.9 | 24.6 | 25.4* | 25.1 | 25.3* | 1.0 |
| Body Fat | 11.4 | 8.4††† | 9.4† | 10.0† | 10.6 | 10.7 | 10.2 | 1.5 |

[a]The combined weights of the gastrocnemius, plantaris, soleus and extensor digitorum longus muscles of both limbs.
The statistical significance of differences are indicated:
Significantly higher than group C, *P < 0.05; P < 0.01; *P < 0.001
Significantly lower than group C, †P < 0.05; ††P < 0.01; †††P < 0.001

SECTION 6

Clenbuterol, a Beta Agonist, Induces Growth in Innervated and Denervated Rat Soleus Muscle via Apparently Different Mechanisms

Summary

Dietary administration of the anabolic agent clenbuterol has already been shown to inhibit or reverse denervation-induced atrophy in rat soleus muscles. We now show that the ameliorative effects of clenbuterol in denervated rat muscles are due principally to a large increase in protein synthetic capacity and a normalised translational efficiency. The responses of innervated and denervated muscles are therefore fundamentally different, the changes in denervated muscles being reminiscent of the classical pleiotypic response of cells to growth factors.

Introduction

Beta-adrenergic agonists have been proposed for use as thermogenic agents to reduce body fat but a limited number of these drugs have an additional anabolic action. Drugs such as clenbuterol, fenoterol and cimaterol, that are effective in this respect are remarkable in having a muscle specific action across a wide range of species. The anabolic action of clenbuterol in innervated rat muscles is expressed as fibre hypertrophy (see Section 1 above) and results primarily from a reduction in protein degradation. We have shown in Section 2 above that in denervated rat soleus muscles undergoing atrophy, due primarily to an elevation in protein degradation, clenbuterol is highly effective at inhibiting or reversing the atrophic response.

This observation suggested that, since the effect of clenbuterol appeared to be mediated by a reduction in degradation, the action of the drug on the growth of denervated muscles would accord with such a mechanism. The present experiment was designed to examine this possibility by studying the changes in protein turnover in denervated rat soleus muscles exposed to clenbuterol.

Materials and Methods

Animals and Experimental Protocol

Two identical experiments were carried out, one for determination of protein turnover, the other for histochemical analysis. For each experiment male Hooded Lister rats of the Rowett strain were weaned at 19 d post partum and divided into 11 groups of 6 animals of equal mean weight. The initial feeding regime was exactly as described previously in Section 1 above. Rats (60±2 g body weight), 6 days post weaning (19 d), which had been accustomed to the control diet PW3 for 3 days were subjected to unilateral removal of 0.7–1.2 cm of sciatic nerve, under ether anaesthesia and aseptic conditions. The animals were housed singly in flat bottomed cages and their body weights recorded daily. At 10 am on day 4 part denervation the rats were offered to appetite control diet (5 groups) or diet containing the beta-adrenergic agonist, clenbuterol (2 mg/kg; 5 groups). One group of rats was analysed as a zero time control and then one group from each of the control and plus-clenbuterol groups were analysed after 12, 24, 36, 72 and 168 h.

The animals were killed and the soleus muscles from both the innervated and denervated limbs removed and frozen suitably for the subsequent analysis (see below).

Determination of the fractional rate of protein synthesis and muscle protein and RNA contents The fractional rate of protein synthesis ($K_s$) was determined, using a flooding dose of 150 mM tritium-labelled 2,6-$^3$H-Phenylalanine (75 microCuries/ml; 1 ml per rat), in both the innervated and denervated soleus muscles of control and clenbuterol treated rats. Unanaesthetised rats were immobilised, by wrapping in a J-cloth, and the large dose of $^3$H-Phenylalanine was injected into a lateral tail vein. After exactly 10 minutes the animals were killed and the hind limbs removed. The legs were rapidly skinned and cooled in iced water before the soleus muscles were dissected and frozen and stored in liquid nitrogen. Muscles were homogenised and prepared for measurement of the specific radioactivity of free and protein-bound phenylalanine. Total protein synthesis was calculated as $K_s \times$protein content.

Muscle protein and RNA contents were determined by known methods.

The fractional rate of degradation was estimated as the difference between $K_s$ and the fractional rate of protein gain ($k_g$). The latter was estimated from the change in protein content during successive time points and assumes the rate to have been linear.

Histochemistry

The histochemical analysis of muscle sections was carried out exactly as described in Section 2 above.

Statistics

Data were assessed by analysis of variance procedures using a split plot design. Where appropriate, comparisons between effects were made using the t-statistic derived from the standard error of the difference (S.E.D.; 36 degrees of freedom).

Results

Sciatic denervation led to a near cessation of soleus growth with the muscle protein mass (Table 1) and fibre areas changing little over the period studied. The presence of clenbuterol in the diet stimulated the growth of both the innervated and denervated muscles (Table 1) but, as we have shown in Section 2 above, denervated muscles showed a relatively greater proportional improvement in protein mass, 71% for denervated versus 25% for innervated, when compared to appropriate controls (P<0.001). The nature of the compositional changes induced by clenbuterol was influenced by nerve status. In innervated muscles both protein and RNA mass increased in proportion (Table 1), while in the denervated muscles the RNA/protein ratio was significantly elevated (P<0.01) by day 1 and remained so until day 3 of exposure to clenbuterol.

By 4 d of denervation the classical changes in protein metabolism were established with both total and fractional rates of protein synthesis ($K_s$) depressed (by 60% and 29% respectively) and fractional rate of degradation ($K_d$) augmented (Table 2). The fibres in these denervated muscles were characteristically small (see Section 2 above). Administration of the drug at this time produced striking differences in effects on protein metabolism between innervated and denervated muscles (Table 2). In both cases clenbuterol produced a rapid decrease in $K_d$ of approximately 50% over the first 24 hours (Table 2) and this was followed by a lesser reduction (15%) for the remaining 6 d (Table 2). In innervated muscles the drug did not influence the $K_s$ (Table 2), and the increase in fibre size could be accounted for by the decrease in protein catabolism. In contrast, denervated muscles exposed to clenbuterol showed a stimulation in the $K_s$ and an improvement in the translational efficiency (g protein synthesised per g RNA) compared to untreated denervated muscles (Table 2). Hence the increase in fibre size was, in part, accounted for by the stimulation in synthesis and in part by the reduction in degradation. After 7 d of clenbuterol administration the denervated muscles exhibited compositional and kinetic properties similar to those of normal innervated muscles of that size.

Discussion

The characteristic anabolism in response to clenbuterol was once again observed in the innervated muscles. In these muscles the increase in fibre size and protein gain (Table 1) associated with the drug treatment could be accounted for by a decrease in protein catabolism (Table 2). In the case of the denervated muscles (Tables 1, 2) only half of the protein anabolism was achieved through reduced degradation, the remainder resulted from a stimulation in both the fractional (Table 2) and total rate of protein synthesis. This arose from changes in two processes which showed different temporal sequences. First, the translational efficiency, which was depressed by 25% as a result of denervation, was restored within 12–24 h of starting clenbuterol treatment to that of control values (Table 2). Second, RNA accretion, and thus total potential translational capacity, was enhanced over the period 24–72 h. In consequence of these two effects, an increase between 24–36 h of 58% in the fractional rate of protein synthesis was observed compared with non-treated denervated muscles and the increase was still significant at 72 h (22%; P<0.05).

Interestingly, previous experiments found a significant (34%) increase in $K_s$ in normal, innervated gastrocnemius muscles from mature rats injected with clenbuterol. No such change in $K_s$ was observed in the present study. The previous experiments differed from the present study in several respects such as animal age, mode of administration and dose of clenbuterol, and in particular the time-interval after drug administration at which $K_s$ was measured. It has been suggested that it is the latter difference, measurement of $K_s$ coinciding with the peak of the thermogenic response within 1 hr of the daily injection, which accounts for the difference in data.

It might be argued that the difference in response of innervated and denervated muscle to clenbuterol was associated with increased numbers of beta-adrenergic receptors in the denervated muscle membrane. This does not, however, appear to be the case. Even in the presence of the mixed beta-antagonist propranolol (2 mg/d equivalent to 100×excess of clenbuterol, a dose which has been shown to block the cardiac hypertrophy and the reduction in body fat), clenbuterol remains effective in reversing the muscle protein loss following denervation.

A factor from sciatic nerve has been identified, which, when injected intramuscularly, will stimulate the growth of denervated muscles. Although it is tempting to speculate that the effects of clenbuterol on denervated muscle might in some way be mediated by this myotrophic factor this is clearly an inadequate explanation for the protein anabolic actions of the drug. For example, the previously isolated myotrophic factor was without effect on innervated muscle whereas clenbuterol, in functionally innervated muscle, is markedly anabolic through alterations in protein breakdown. The changes in translational efficiency and capacity in clenbuterol treated denervated muscles are however similar to the responses of other cell types to specific peptide growth factors. Restoration of translational efficiency has been observed as a response to many stimuli, including refeeding after fasting, and there may be several or indeed many signals which can be recognised. In normal muscles one such signal may be produced from the functional nerve which fully activates the system. Further stimuli induced either directly or indirectly by clenbuterol may selectively alter proteolysis.

In conclusion we have demonstrated that the novel response of denervated muscle to the beta-agonist clenbuterol involves at least two mechanisms. The first involves, in the down-regulated denervated state, changes in translational efficiency and capacity which are reminiscent of the classical pleiotypic responses of cells to growth factors. The second is a specific reduction in protein breakdown. In the innervated state the first effect is not observed because the muscles have already responded to other stimuli, whereas the second is manifested. Many other physiological stimuli enhance protein gain through mechanisms which stimulate primarily protein synthesis but also degradation. However, the special characteristics of clenbuterol, and its analogues, appear to offer exciting advances both in manipulating muscle composition and growth as well as being potentially valuable tools in the study and treatment of myogenic disorders.

TABLE 1

(Section 6):
Compositional effect of clenbuterol on
innervated and denervated rat soleus muscle

| Day after | Innervated limb | | Denervated limb | |
|---|---|---|---|---|
| Clenbuterol | Control | + Clen. | Control | + Clen. |
| | Protein content (mg) | | | |
| 0 | 5.3 | | 3.0*** | 3.5* |
| 0.5 | 5.7 | 5.6 | 3.2*** | 3.5* |
| 1.0 | 6.1 | 6.3 | 3.4*** | 3.5** |
| 1.5 | 6.1 | 6.1 | 2.9*** | 3.6*, + |
| 3.0 | 6.7 | 7.3+ | 3.0*** | 3.9**, ++ |
| 7.0 | 9.7 | 12.1+++ | 3.5*** | 6.0***, +++ |

S.E.D. for effect of clenbuterol 0.3082
S.E.D. for effect of nerve status 0.2425

| | RNA content (µg) | | | |
|---|---|---|---|---|
| 0 | 94 | | 52*** | |
| 0.5 | 92 | 93 | 61*** | 66*** |
| 1.0 | 104 | 104 | 61*** | 72***, + |
| 1.5 | 100 | 106 | 52*** | 86***, +++ |
| 3.0 | 108 | 121+ | 56*** | 91***, +++ |
| 7.0 | 132 | 162+++ | 60*** | 98***, +++ |

S.E.D. for effect of clenbuterol 5.574
S.E.D. for effect of nerve status 5.170

| | RNA Protein (µg/mg) | | | |
|---|---|---|---|---|
| 0 | 17.5 | | 17.4 | |
| 0.5 | 16.1 | 16.5 | 19.0* | 18.7 |
| 1.0 | 17.1 | 16.5 | 18.4 | 22.5***, ++ |
| 1.5 | 16.2 | 17.3 | 18.0 | 23.6***, +++ |
| 3.0 | 16.1 | 16.5 | 18.99* | 23.4***, ++ |
| 7.0 | 13.6 | 13.4 | 17.1** | 16.4* |

S.E.D. for effect of clenbuterol 1.389
S.E.D. for effect of nerve status 1.222
For effect of clenbuterol +++$p < 0.005$, ++$p < 0.01$, +$p < 0.05$
For effect of nerve status *$p < 0.005$, $p < 0.01$, *$p < 0.05$
(Protein and RNA contents and the ratio RNA:protein in the innervated and denervated soleus muscles of rats subjected to unilateral sciatic denervation)

TABLE 2

(Section 6)
Metabolic effects of clenbuterol on innervated and denervated
rat soleus muscle

| Day after | Innervated limb | | Denervated limb | |
|---|---|---|---|---|
| Clenbuterol | Control diet | + Clenbuterol | Control diet | + Clenbuterol |
| | $K_s$ (%/day) | | | |
| 0 | 27.7 | | 19.8*** | |
| 0.5 | 29.3 | 26.5 | 21.9** | 25.9 |
| 1.0 | 24.6 | 23.8 | 20.3 | 32.4***, +++ |
| 1.5 | 25.1 | 27.1 | 23.5 | 36.6***, +++ |
| 3.0 | 27.1 | 27.1 | 25.8 | 31.6+ |
| 7.0 | 18.1 | 19.6 | 18.6 | 21.8 |

S.E.D. for effect of clenbuterol 2.691
S.E.D. for effect of nerve status 2.279

| | $K_s$/RNA (g prot. synthesised/g RNA) | | | |
|---|---|---|---|---|
| 0 | 16.5 | | 11.2*** | |
| 0.5 | 18.1 | 16.0 | 11.9*** | 14.1 |
| 1.0 | 14.4 | 14.3 | 11.1* | 14.5++ |
| 1.5 | 15.7 | 15.9 | 13.2 | 15.4 |
| 3.0 | 16.9 | 16.6 | 14.8 | 13.6* |
| 7.0 | 13.4 | 14.6 | 10.9 | 13.3* |

S.E.D. for effect of clenbuterol 1.732
S.E.D. for effect of nerve status 1.262

TABLE 2-continued (Section 6)
Metabolic effects of clenbuterol on innervated and denervated rat soleus muscle

| Day after Clenbuterol | Innervated limb | | Denervated limb | |
|---|---|---|---|---|
| | Control diet | + Clenbuterol | Control diet | + Clenbuterol |

$K_g$ and calculated $K_d$

| | Innervated limb | | | | Denervated limb | | | |
|---|---|---|---|---|---|---|---|---|
| | $K_g$ Control diet | $K_d$ | $K_g$ + Clenbuterol | $K_d$ | $K_g$ Control diet | $K_d$ | $K_g$ + Clenbuterol | $K_d$ |
| 0–1 d | 14.0 | 13.2 | 17.2 | 8.6 | 0 | 20.7 | 15.4 | 10.6 |
| 1–3 d | 9.5 | 16.1 | 14.7 | 11.3 | 0 | 23.2 | 11.4 | 22.1 |
| 3–7 d | 11.0 | 11.6 | 12.4 | 11.0 | 0 | 22.2 | 10.9 | 15.8 |
| For the effect of clenbuterol | | | +++p < 0.005 | | | ++p < 0.01 | +p < 0.05 | |
| For the effect of nerve status | | | ***p < 0.005 | | | **p < 0.01 | *p < 0.05 | |

(The fractional rate of protein synthesis ($K_g$) in both the innervated and denervated soleus muscles of the same rats as described in Table 1. The fractional rate of protein deposition ($K_g$) was based on the change in muscle protein between the periods specified. The fractional rate of protein degradation ($K_d$) was estimated as the difference between the mean values of $K_g$ and $K_s$. It was assumed that the small amount of growth in the denervated limbs of control fed rats was not significantly different from zero. The resultant value is taken to be an indication of the rate of protein degradation in these muscles over the time period specified.)

SECTION 7

The Effect of Clenbuterol on Clinical Course and Nitrogen Balance in Patients with Cancer Cachexia Background Clenbuterol is a beta(2) sympathomimetic drug which has been used in the treatment of bronchospasm in animals and man. Clinical trials have shown a similar efficacy and side-effect profile to salbutamol or terbutaline which are the most popular beta(2) agonists in use in the United Kingdom (where clenbuterol is not currently available for clinical use).

Recent work has shown that clenbuterol has three additional effects on muscle protein which are not seen with salbutamol or terbutaline. Firstly clenbuterol can specifically increase the rate of skeletal and cardiac muscle growth in young animals; there is a slight reduction in growth rate of the viscera of drug-treated animals with respect to control animals. Secondly clenbuterol limits the atrophy of skeletal muscle in denervated limbs in rats. Thirdly in animals treated with clenbuterol after the development of denervation atrophy, reversal of the atrophic changes occur with a simultaneous increase in contractile strength.

The need for a drug which can selectively promote growth or limit otherwise irresistible wasting exists in many pathological situations affecting enormous numbers of patients and it is therefore important that potential clinical applications of the protein anabolic effects of clenbuterol are made available at the earliest proof of efficacy. Of particular importance in relation to maintenance of muscle mass is the observation that loss of lean body tissue to approximately 80–85% of the ideal figure almost always results in a fatal outcome. This situation is frequently encountered in patients with neoplastic disease and associated cachexia with its attendant muscle weakness. Treatment at this stage has little to offer other than analgesia but patients in this position could benefit in terms of subjective well-being and longer survival if lean tissue wasting could be slowed or arrested by a drug such as clenbuterol. In view of the slight limitation on visceral growth there is no indication that tumour growth would be enhanced by the drug and indeed there is a possibility that it may be reduced due to the preferential anabolic effect on skeletal muscle.

Outline of Proposed Proof of Efficacy of Clenbuterol

A preliminary study of the effect of clenbuterol in cancer cachexia is hereby proposed. In the first instance such a study would have to be simple in design and objectives as it would be unethical to subject terminally ill patients to arduous investigation without more positive evidence of likely therapeutic benefit. Nevertheless it is important that the study is carried out and it should not prove difficult for the suppliers of clenbuterol to obtain the necessary Clinical Trial Exemption Certificate from the Committee for the Safety of Medicines to allow the use of clenbuterol in a group of patients who have little to lose and possibly much to gain. This certification would then allow an approach to the relevant Ethical Committee who are likely to approve the proposed protocol. Due to the varied clinical forms, manifestations and disease course in patients with established malignancy it would be necessary to study reasonable numbers of patients (say 30–40) in order to allow a useful assessment of use of clenbuterol in practice. Patients with solid tumours, a documented weight loss of more than 10% and who are receiving only palliative therapy would be studied. The study design would be dual with an initial parallel, placebo-controlled phase followed, for those who are willing and able to continue by a second crossover phase. Those entering the study would have a 3-day run-in period before randomisation to receive either clenbuterol 20 microgrammes three times daily or placebo for 7 days followed by a 7-day washout period; those able to continue would then take placebo or clenbuterol for a further 7 days finishing with a 3-day run-out period. Protein wasting would be assessed simply by measurement of daily urinary nitrogen losses throughout the study. Clinical assessment, diagnostic classification, previous and current therapy would be noted. Dietary diaries would be kept to monitor any changes in food intake during the study, subjective assessment of well-being and debility made using visual analogue scales and any adverse effects of trial medication recorded. In addition, when appropriate to each patient's condition, simple tests of active muscle function could be made at intervals throughout the study. Basic anthropometric measurements (height, weight and skinfold thickness) would also be recorded at intervals.

The current incidence of cancer cachexia in the available population would enhance completion of the study within approximately 12 months.

SECTION 8

The Effect of Clenbuterol on Skeletal Muscle Development in Rowett Hodded Lister Rats Background Previous studies in rats have demonstrated that the effects of clenbuterol are influenced or determined by the physiological state of the muscle or its fibre type. In several respects (eg membrane properties, isozyme patterns, protein turnover rates) denervated muscle has similarities with that of the foetus or neonate. Our studies have shown that clenbuterol was particularly effective as an anabolic agent in denervated muscle. The response was of greater magnitude and more rapid than in innervated, growing, fully differentiated muscle. Furthermore, the mechanism by which this response was elicited was also different from that in innervated muscle. Whereas clenbuterol gave rise to little or no change in the fractional rate of protein synthesis in normal innervated muscle, its effect on denervated muscle was to normalise translationed efficiency (g protein synthesised/g RNA) and significantly increase the fractional rate of protein synthesis. These data suggest that the undifferentiated or immature muscle may be particularly responsive to exposure to beta-two agonists, or more specifically clenbuterol and its analogues. It is well documented that the foetus is sensitive to specific signals at particular stages of development, eg single dose or short term administration of gonadotrophins to neonatal rats can produce marked changes in body composition which persist through to adulthood. If clenbuterol exerts its muscle-specific effects by altering the fundamental properties of the muscle (for example at the plasma membrane) then modifications induced early in development may be persistent. An investigation of such a possibility requires that the drug (or active factor associated with the drug administration) crosses the placenta for foetal imprinting or is secreted in the milk for dosing the neonate.

Thus the aim of this work was to examine the effect of clenbuterol on skeletal muscle development and to assess the possibility that interference with the early pattern of development may result in a permanent alteration of the growth pattern.

Two areas of focus were chosen:
a. Ante-natal muscle development
b. Muscle development from birth to post-weaning
c. Antenatal Development in Soleus and EDL Muscles of Rats It is well established that the temporal sequences of events during myogenesis is of crucial importance in establishing the genetic expression of the individual muscle cells, and hence the muscle as a whole. Myotubes start to form in the foetus at around 15 d gestation, a time at which there are few neural contacts. The first experiment was therefore designed to expose the foetus to clenbuterol from 12 d gestation and to sample the muscles at 19 d gestation, at which time neuromusclar junctions can be found and the muscle is beginning to mature.

Pregnant dams (mother animals) were fed control diet plus clenbuterol (2 mg/kg) from 12 d gestation. Whole single soleus and EDL muscles were isolated from the 19 d foetuses and examined at both light and electron microscopic levels. Muscles from clenbuterol-treated foetuses possessed primitive differentiated motor endplates on both primary and secondary generation myotubes. In control muscles, however, it was not common to find endplates on secondary generation myotubes. Moreover, it was evident that in the clenbuterol-treated myotubes fusion had occurred to a greater extent than in the controls. The myofibrillar proteins showed a greater degree of spatial organisation, and the tubular systems appeared to be more extensively organised than in controls.

Overall, the microscopic results indicated that clenbuterol treatment of foetal rat muscle in utero had resulted in the advancement of muscle fibre fusion. This contention was supported by the biochemical analyses. Since single muscles were too small for accurate assessments, determinations were made on the whole posterior distal muscle group.

The major results were:
i. The drug increased the weight ($P<0.05$) and protein content ($P<0.01$) of the foetal hearts.
ii. Skeletal muscle wet weights, and protein content and concentrations were significantly ($P<0.005$) reduced in clenbuterol-treated foetuses compared to the controls.
iii. DNA concentration was significantly ($P<0.005$) elevated in clenbuterol-treated groups, but RNA concentration was not significantly different from control values.
iv. Both total RNA and DNA contents were significantly ($P<0.005$) reduced.

These results, while supporting the concept that clenbuterol treatment advances fusion of myoblasts, need to be interpreted with caution.

Unexpectedly a considerable anabolic effect of clenbuterol was observed in the pregnant dams. Thus it is possible that some penalty was directed at the foetuses; and in particular at the foetal skeletal muscle since the agonist effect on heart weight is expressed as in weaning animals.

In the dams it was found that:
i. there was a 15–30% increase in weight of individual muscles (as a fraction of body weight) in the clenbuterol-treated dams with respect to the controls.
ii. the heart weights were increased in the treated animals by 10–20%.

However, there was no significant differences with respect to either mean foetal number or mean foetal weight between control and clenbuterol fed groups.

These results then suggested that clenbuterol was accelerating myotube formation at the expense of cell division. It was therefore important to establish the effect of clenbuterol on muscle fibre number. Consequently a further set of experiments were carried out to examine the effect of continuous exposure to the drug from 12 d gestation through parturition to weaning. We observed that while the presence of clenbuterol in the diet did not inhibit the final outcome or success of parturition, the onset of labour was delayed by approximately 12 hours in comparison with control dams.

As with dams killed prior to parturition, dams fed clenbuterol until weaning showed an increase in heart weight of approximately 7% and in muscle weight of 20–30%.

As before, pregnant dams were fed diet containing clenbuterol (2 mg/kg). After parturition litters were adjusted to 8 pups (4 of each sex) and the pups maintained with their mothers until weaning. The results from the weanling rats exposed to clenbuterol continuously from 12 d gestation were particularly interesting. As observed in the study of foetal muscle, treatment with clenbuterol resulted in a significant reduction in muscle weight. Histological examination, however, revealed that there was a significant ($P<0.05$) reduction in total fibre number in both soleus and EDL muscles from treated animals. Furthermore the cross-sectional area of these fibres was considerably greater than those from control animals. These results were in contracts to those from weanling rats exposed to clenbuterol for 4 days only: the fibre hypertrophy was not accompanied by a reduction in fibre number.

Thus, this data together with that from the foetuses indicated that:

i. clenbuterol was accelerating myotube/myofibre formation at the expense of cell division;

ii. as a result of which, there appeared to be a permanent change in fibre number and size;

iii. in other words that clenbuterol has two effects:

1. in foetal muscle it alters fibre number, presumably under genotypic control; and
2. in adult muscle it alters fibre size, presumably under phenotypic control.

b. Effects of Neonatal Exposure

The observations made with animals exposed first to Clenbuterol in utero showed the common pattern of increased fusion and reduced fibre number. In consequence these two effects approximately cancelled out, so the pups did hot show a muscle weight or protein anabolic response as observed for post-weaning animals.

One hypothesis that follows from this is that Clenbuterol acts through a single system, which has a developmental aspect, and that muscle gain is related to maturity; either of the muscle or associated receptor populations or of the nerve supply. A second hypothesis is that the foetal/neonatal and the post-weaning responses do, in fact, reflect Clenbuterol interaction with two, at least, different mechanisms.

It was therefore appropriate to examine the stage at which the rat becomes sensitive to Clenbuterol, when assessed in terms of muscle protein anabolism. In the first study attempted, pups were born to dams maintained on control diet. Litters were adjusted to 8 pups (4 of each sex), and half the mothers transferred to control diet plus Clenbuterol (2 mg/kg). At 18 days the pups were analysed. Pups from dams given Clenbuterol were 9% lighter than controls while absolute muscle weights were decreased by 11–13%. On a body weight basis heart mass was increased by 7% while liver size decreased by 7%. In plantaris muscles total protein from Clenbuterol-treated animals were lower by 7%, RNA was unaltered while DNA was decreased by 10% Essentially similar data were obtained for soleus muscle.

This experimental design assumed that, first, Clenbuterol would be made available to the pups from the milk of the dam in sufficient quantities and, second, that the drug would not alter the lactational output. In practice the slight effect on relative heart mass did indicate that some Clenbuterol, at lest, was made available through the mammary gland. However, from the daily weights of pups it was clear that there was a major check in growth during the first 48 h that the dams received the drug - this was probably due to reduced milk secretion (the intake of dams declined during this short period). Furthermore, analysis of the dams for body composition at the end of the study showed, as for the pregnant state, that muscle growth was promoted by a 4–12% in Clenbuterol-treated animals; heart mass was unaltered. Clenbuterol thus appeared to have over-ridden, at least partially, the supply of nutrients to the mammary gland. As blood flow, and thus probably heart size, is already elevated during lactation a potential re-distribution to other tissues might be achieved without a net increase in overall cardiac output and without the requirement for elevated heart mass.

These findings indicated a different experimental approach was required. In consequence, rather than including the drug within the diet of the mother, pups were dosed orally, twice a day, with appropriate amounts of Clenbuterol (fixed as 200 microgrammes/kg body weight; this is the same as used in the growth studies described in a previous section above). The design of the experiment was otherwise similar to the above antenatal experiment, ie litters culled to 8 (4 of each sex) and then at staggered intervals from 4 days onwards half the litter (2 of each sex) received Clenbuterol while the other half received vehicle (water). This design was to reduce scatter due to inter-litter variation. Two litters were applied to each treatment, in which Clenbuterol was administered from either day 4, day 8, day 12, day 16 or day 19 (weaning) and all pups were analysed at day 25.

No differences in body weight were found. All Clenbuterol-treated animals showed increases in heart weight (9–15%). Only in animals given the drug from day 19 onwards were differences in muscle weight (+10%) observed. Previous treatment, ie dosage at times between days 4–25 and days 16–25 had no effect on muscle weight. Muscle protein content, however, was increased equally with all treatments from day 8 onwards (magnitude of increase 11–13%). Total RNA was unaffected by Clenbuterol but, in common with the foetal studies, there were again significant reductions ($P<0.01$) in DNA content. For animals receiving the drug at 16 days or earlier the decrease was 9–13%, whereas with treatment at days 19–25 the decline was only 5%.

The effect on protein gain, therefore, was occurring most actively during the immediate post-weaning period (days 19–25) and that earlier exposure did not make a significant contribution. Two explanations could account for these observations.

1. The earlier exposure had occurred at a time in which the mechanism leading the muscle protein gain was inactive. Alternatively the system may have been present, but inactive, and was desensitised or down-regulated by early exposure to the drug.

2. The promotion of early fibre fusion, noted for embryonic muscle, continued in early to late suckling with consequent larger fibres but fewer in number so that the potential for extra muscle growth was limited.

This experiment has been repeated, in order to focus on the temporal sequence of events involved. The design was in principle that illustrated above, but now the time intervals of exposure were altered to 2 day increments, applied from days 14–24 with all animals analysed at day 28. Again maximum responses were observed for animals treated from either day 20 or day 22, it was reduced with treatment from day 24–28. Responses for animals dosed from day 14 to day 18 were 50–100% lower than the optimal growth of muscle protein mass. Heart weight increases (16–24%) were similar for all groups.

This experiment again confirms that the weaning period represents a time of great sensitivity for the anabolic action of the drug. At this stage of development considerable changes occur in gut morphology and metabolism. In addition, muscle tissue also becomes especially sensitive to specific hormones involved in the regulation of protein metabolism, for example, the glucocorticoids. The potential interaction of Clenbuterol with either systemic or gut hormones needs to be investigated further.

While the above experimental information refers particularly to rats, it is considered possible that the same or similar effects would be observed in other mammalian animals and in humans, and possibly to a certain extent in non-mammalian animals.

I claim:

1. A method of alleviating or reversing loss of function of striated muscle arising from at least one illness in the group of illnesses consisting of:
  a) muscle disease;
  b) peripheral nervous system disease;
  c) central nervous system disease;
  d) a humorally mediated catabolic state;
  e) muscular trauma arising from accident;
  f) muscular trauma arising from surgery; and
  g) muscular atrophy arising from temporary disuse,
  wherein said method comprises the step of administering an effective amount of a beta-adrenergic agonist and a suitable carrier or diluent,
  wherein said beta-adrenergic agonist is other than clenbuterol, an acid addition salt of clenbuterol or an analog thereof.

2. A method as claimed in claim 1 wherein said beta-adrenergic agonist is selected from the group consisting of fenoterol, salbutamol, orciprenaline, isoetharine, cimaterol, ractopamine, reproterol, terbutaline, the acid addition salts thereof, the analogs thereof and mixtures thereof.

3. A method of alleviating or reversing loss of function of striated muscle arising from a humorally mediated catabolic state wherein said method comprises the step of administering an effective amount of a beta-adrenergic agonist and a suitable carrier or diluent,
  wherein said beta-adrenergic agonist is other than clenbuterol, an acid addition salt of clenbuterol or an analog thereof.

4. A method as claimed in claim 3 wherein said beta-adrenergic agonist is selected from the group consisting of fenoterol, salbutamol, orciprenaline, isoetharine, cimaterol, ractopamine, reproterol, terbutaline, the acid addition salts thereof, the analogs thereof and mixtures thereof.

5. A method as claimed in either one of claims 1 and 3 wherein the humorally mediated catabolic state is cachexia.

6. A method as claimed in claim 5 wherein the cachectic condition is caused by cancer.

7. A method as claimed in claim 5 wherein the cachectic condition is caused by sepsis.

8. A method as claimed in claim 1 wherein the alleviation or reversal of loss of function comprises alleviation or limitation of muscular atrophy arising from temporary disuse caused by neurological disease or immobilisation.

* * * * *